(12) United States Patent
Alexander et al.

(10) Patent No.: US 8,168,634 B2
(45) Date of Patent: May 1, 2012

(54) THIAZOLE DERIVATIVES AS KINASE INHIBITORS

(75) Inventors: Rikki Peter Alexander, Slough (GB); Julien Alistair Brown, Slough (GB); Karen Viviane Lucile Crépy, Slough (GB); Stephen Robert Mack, Slough (GB)

(73) Assignee: UCB Pharma S.A., Brussels (BE)

( * ) Notice: Subject to any disclaimer, the term of this patent is extended or adjusted under 35 U.S.C. 154(b) by 184 days.

(21) Appl. No.: 12/446,140

(22) PCT Filed: Oct. 16, 2007

(86) PCT No.: PCT/GB2007/003949
§ 371 (c)(1),
(2), (4) Date: Jun. 4, 2010

(87) PCT Pub. No.: WO2008/047109
PCT Pub. Date: Apr. 24, 2008

(65) Prior Publication Data
US 2010/0298310 A1    Nov. 25, 2010

(30) Foreign Application Priority Data

Oct. 19, 2006  (GB) .................................. 0620818.5

(51) Int. Cl.
*A61K 31/535* (2006.01)
*C07D 413/04* (2006.01)
*C07D 413/14* (2006.01)

(52) U.S. Cl. .................. 514/235.2; 514/236.8; 544/133; 544/143

(58) Field of Classification Search .................. 544/133, 544/143; 514/235.2, 236.8
See application file for complete search history.

(56) References Cited

FOREIGN PATENT DOCUMENTS

| WO | WO2004078754 | 9/2004 |
| WO | WO2004096797 | 11/2004 |
| WO | WO2006051270 | 5/2006 |
| WO | WO2006114606 | 11/2006 |
| WO | WO2007138110 | 12/2007 |

OTHER PUBLICATIONS

Byrn et al., Solid-State Chemistry of Drugs, 2nd Ed., SSCI, Inc., West Lafayette, IN, Ch. 11, pp. 233-247 (1999).*
Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*
International Search Report dated Feb. 4, 2008.

* cited by examiner

*Primary Examiner* — Rebecca Anderson
(74) *Attorney, Agent, or Firm* — McDonnell Boehnen Hulbert & Berghoff LLP

(57) ABSTRACT

A series of thiazole derivatives which are substituted in the 2-position by a substituted morpholin-4-yl moiety, being selective inhibitors of P13 kinase enzymes, are accordingly of benefit in medicine, for example in the treatment of inflammatory, autoimmune, cardiovascular, neurodegenerative, metabolic, oncological, nociceptive or ophthalmic conditions.

7 Claims, No Drawings

THIAZOLE DERIVATIVES AS KINASE INHIBITORS

The present invention relates to a class of substituted thiazole derivatives, and to their use in therapy. More particularly, the invention provides a family of thiazole derivatives which are substituted in the 2-position by a substituted morpholin-4-yl moiety. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., Chemistry & Biology, 2003, 10, 207-213; and S. G. Ward & P. Finan, Current Opinion in Pharmacology, 2003, 3, 426-434); and are known to be involved in the pathology of cancer, and metabolic, inflammatory and cardiovascular diseases (cf. M. P. Wymann et al., Trends in Pharmacol. Sci., 2003, 24, 366-376). Aberrant upregulation of the PI3K pathway is implicated in a wide variety of human cancers (cf. S. Brader & S. A. Eccles, Tumori, 2004, 90, 2-8).

The compounds in accordance with the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds in accordance with the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

WO 2004/071440 describes a class of thiazolyl-based compounds that are stated to be useful for treating p38 kinase-associated conditions. However, none of the compounds disclosed in that publication corresponds to a compound of the present invention; and there is no disclosure nor any suggestion in that publication that the compounds described therein have any affinity for human PI3K enzymes.

The compounds in accordance with the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The present invention provides a compound of formula (I), or a pharmaceutically acceptable salt or solvate thereof:

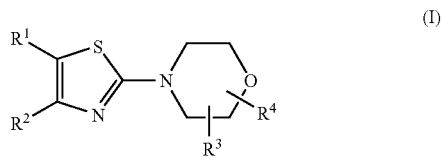

(I)

wherein $R^1$ represents —$COR^a$ or —$CONR^bR^c$;

$R^a$ represents $C_{1-6}$ alkyl or hydroxy;

$R^b$ represents hydrogen, $C_{1-6}$ alkyl, $C_{3-7}$ cycloalkyl or $C_{3-7}$ cycloalkyl($C_{1-6}$)alkyl;

$R^c$ represents hydrogen or $C_{1-6}$ alkyl;

$R^2$ represents hydrogen, $C_{1-6}$ alkyl, halogen, cyano or trifluoromethyl;

$R^3$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; and $R^4$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl, $C_{5-7}$ heterocycloalkyl or heteroaryl, any of which groups may be optionally benzofused and/or substituted by one or more substituents.

Where any of the groups in the compounds of formula (I) above is stated to be optionally substituted, this group may be unsubstituted, or substituted by one or more substituents. Typically, such groups will be unsubstituted, or substituted by one or two substitutents. Suitably, such groups will be unsubstituted or monosubstituted.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl and 2,2-dimethylpropyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Specific aryl($C_{2-6}$)alkenyl groups include 2-phenylethenyl and 3-phenylprop-2-en-1-yl.

A specific aryl($C_{2-6}$)alkynyl group is 3-phenylprop-2-yn-1-yl.

Particular biaryl groups include biphenyl and naphthylphenyl.

Suitable heterocycloalkyl groups, which may comprise benzo-fused analogues thereof, include azetidinyl, tetrahydrofuranyl, pyrrolidinyl, indolinyl, imidazolidinyl, tetrahydropyranyl, piperidinyl, 1,2,3,4-tetrahydroquinolinyl, 1,2,3,4-tetrahydro-isoquinolinyl, piperazinyl, 1,2,3,4-tetrahydroquinoxalinyl, morpholinyl and thiomorpholinyl.

Suitable heteroaryl groups include furyl, benzofuryl, dibenzofuryl, thienyl, benzothienyl, pyrrolyl, indolyl, pyrrolo[2,3-b]pyridinyl, pyrazolyl, indazolyl, oxazolyl, isoxazolyl, thiazolyl, isothiazolyl, imidazolyl, imidazo[1,2-a]pyridinyl, benzimidazolyl, oxadiazolyl, thiadiazolyl, triazolyl, benzotriazolyl, tetrazolyl, pyridinyl, quinolinyl, isoquinolinyl, pyridazinyl, pyrimidinyl and pyrazinyl groups.

The term "halogen" as used herein is intended to include fluorine, chlorine, bromine and iodine atoms, especially fluoro or chloro.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C{=}O$)-enol ($CH{=}CHOH$) tautomers. Formula (I) and the formulae depicted hereinafter are intended to represent all individual tautomers and all possible mixtures thereof, unless stated or shown otherwise.

Specific sub-classes of compounds in accordance with the present invention are represented by the compounds of formula (IA) and (IB):

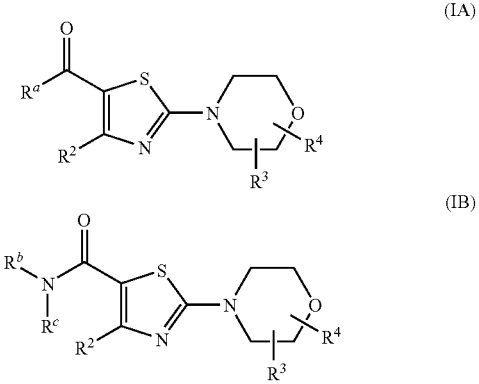

wherein $R^a$, $R^b$, $R^c$, $R^2$, $R^3$ and $R^4$ are as defined above.

In one embodiment, $R^1$ represents —$COR^a$. In another embodiment, $R^1$ represents —$CONR^bR^c$.

In one embodiment, $R^a$ represents $C_{1-6}$ alkyl, especially methyl. In another embodiment, $R^a$ represents hydroxy.

Suitably, $R^a$ represents methyl.

Typically, $R^b$ represents hydrogen, $C_{1-6}$ alkyl or $C_{3-7}$ cycloalkyl. Suitably, $R^b$ represents hydrogen or $C_{3-7}$ cycloalkyl. In one embodiment, $R^b$ represents hydrogen. In another embodiment, $R^b$ represents $C_{1-6}$ alkyl, especially methyl. In a further embodiment, $R^b$ represents $C_{3-7}$ cycloalkyl, especially cyclopropyl. In an additional embodiment, $R^b$ represents $C_{3-7}$ cycloalkyl($C_{1-6}$)alkyl, especially cyclopropylmethyl.

In a particular embodiment, $R^c$ represents hydrogen. In another embodiment, $R^c$ represents $C_{1-6}$ alkyl, especially methyl.

Particular values of $R^1$ include acetyl, carboxy, aminocarbonyl, methylaminocarbonyl, dimethylaminocarbonyl and cyclopropylaminocarbonyl.

Typical values of $R^1$ include acetyl, aminocarbonyl and cyclopropylaminocarbonyl.

In one embodiment, $R^2$ represents hydrogen. In another embodiment, $R^2$ represents $C_{1-6}$ alkyl. In a further embodiment, $R^2$ represents halogen. In a still further embodiment, $R^2$ represents cyano. In an additional embodiment, $R^2$ represents trifluoromethyl.

Suitably, $R^2$ represents $C_{1-6}$ alkyl. A particular value of $R^2$ is methyl.

Typically, $R^3$ represents $C_{1-6}$ alkyl, aryl, aryl($C_{1-6}$)alkyl, aryl-($C_{2-6}$)alkynyl, biaryl($C_{1-6}$)alkyl, $C_{3-7}$ heterocycloalkyl($C_{1-6}$)alkyl, $C_{3-7}$ heterocycloalkyl-carbonyl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

In a representative embodiment, $R^3$ represents $C_{1-6}$ alkyl, aryl($C_{1-6}$)alkyl, biaryl-($C_{1-6}$)alkyl, heteroaryl($C_{1-6}$)alkyl or heteroaryl-aryl($C_{1-6}$)alkyl, any of which groups may be optionally substituted by one or more substituents. Preferably, $R^3$ represents methyl, arylmethyl, biarylmethyl, heteroarylmethyl or heteroaryl-arylmethyl, any of which groups may be optionally substituted by one or more substituents.

In a particular embodiment, $R^3$ represents substituted or unsubstituted indolyl-($C_{1-6}$)alkyl. Advantageously, $R^3$ represents substituted or unsubstituted indolylmethyl.

In a typical embodiment, $R^3$ represents substituted or unsubstituted phenyl-($C_{1-6}$)alkyl. Advantageously, $R^3$ represents substituted or unsubstituted benzyl.

Illustratively, $R^3$ represents methyl, phenyl, benzyl, phenylethyl, naphthylmethyl, phenylpropynyl, biphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, pyrrolo[2,3-b]-pyridinylmethyl, benzimidazolylmethyl, benzotriazolylmethyl, pyridinylmethyl, quinolinylmethyl, isoquinolinylmethyl, benzofurylbenzyl, thienylbenzyl, benzothienylbenzyl, indolylbenzyl, isoxazolylbenzyl, pyrazolylbenzyl, pyridinylbenzyl, pyrimidinylbenzyl or phenylpyridinylmethyl, any of which groups may be optionally substituted by one or more substituents.

Suitably, $R^4$ represents hydrogen or optionally substituted $C_{1-6}$ alkyl.

Examples of typical substituents on $R^3$ and/or $R^4$ include halogen, cyano, nitro, $C_{1-6}$ alkyl, hydroxy($C_{1-6}$)alkyl, trifluoromethyl, pyrazolyl, ($C_{1-6}$)alkylpyrazolyl, di($C_{1-6}$)alkylpyrazolyl, aryl($C_{1-6}$)alkylpyrazolyl, morpholinyl($C_{1-6}$)alkylpyrazolyl, ($C_{1-6}$)alkyl-imidazolyl, ($C_{1-6}$)alkylpyridinyl, pyrimidinyl, aryl($C_{1-6}$)alkyl, hydroxy, $C_{1-6}$ alkoxy, difluoromethoxy, trifluoromethoxy, aryloxy, haloaryloxy, aryl($C_{1-6}$)alkoxy, pyridinyloxy($C_{1-6}$)alkyl, methylenedioxy, difluoromethylenedioxy, $C_{1-6}$ alkylthio, arylthio, $C_{1-6}$ alkylsulphinyl, arylsulphinyl, $C_{1-6}$ alkylsulphonyl, arylsulphonyl, $C_{1-6}$ alkylsulphonyloxy, amino, $C_{1-6}$ alkylamino, di($C_{1-6}$)alkylamino, phenylamino, [($C_{1-6}$)alkyl](phenyl)amino, pyridinylamino, halopyridinylamino, ($C_{1-6}$)alkylpyridinylamino, di($C_{1-6}$)alkylpyridinylamino, ($C_{1-6}$)alkoxypyridinylamino, pyrrolidinyl, morpholinyl, $C_{2-6}$ alkylcarbonylamino, benzofuryl-carbonylamino, $C_{2-6}$ alkoxycarbonylamino, $C_{1-6}$ alkylsulphonylamino, arylsulphonylamino, amino($C_{1-6}$)alkyl, ($C_{1-6}$)alkylamino($C_{1-6}$)alkyl, di($C_{1-6}$)alkylamino($C_{1-6}$)alkyl, pyridinylamino($C_{1-6}$)alkyl, ($C_{1-6}$)alkylpiperazinyl($C_{1-6}$)alkyl, morpholinyl($C_{1-6}$)alkyl, formyl, $C_{2-6}$ alkylcarbonyl, carboxy, $C_{2-6}$ alkoxycarbonyl, aminocarbonyl, $C_{1-6}$ alkylaminocarbonyl, [hydroxy($C_{1-6}$)alkyl]aminocarbonyl, di($C_{1-6}$)alkylaminocarbonyl, [($C_{1-6}$)alkyl]-[hydroxy($C_{1-6}$)alkyl]aminocarbonyl, aryl($C_{1-6}$)alkylaminocarbonyl, benzothienylmethylaminocarbonyl, azetidinylcarbonyl, pyrrolidinylcarbonyl, piperidinylcarbonyl, ($C_{1-6}$)alkylpiperazinylcarbonyl, morpholinylcarbonyl, aminosulphonyl, $C_{1-6}$ alkylaminosulphonyl, di($C_{1-6}$)alkylaminosulphonyl and $C_{2-6}$ alkoxycarbonyloxy. Further examples of typical substituents on $R^3$ and/or $R^4$ include piperidinyl($C_{1-6}$)alkylphenyl, triazolyl, N—($C_{1-6}$)alkyl-N—[($C_{1-6}$)alkylpiperidinyl]amino and trifluoroacetyl.

Particular examples of typical substituents on $R^3$ and/or $R^4$ include halogen, cyano, piperidinyl($C_{1-6}$)alkylphenyl, triazolyl, $C_{1-6}$ alkoxy, trifluoromethoxy, haloaryloxy, methylenedioxy, difluoromethylenedioxy, $C_{1-6}$ alkylsulphonyl, phenylamino, pyridinylamino, N—($C_{1-6}$)alkyl-N—[($C_{1-6}$)alkylpiperidinyl]amino, $C_{2-6}$ alkylcarbonyl, trifluoroacetyl, carboxy, $C_{2-6}$ alkoxycarbonyl and di($C_{1-6}$)alkylaminocarbonyl.

Selected examples of typical substituents on $R^3$ and/or $R^4$ include halogen, trifluoromethoxy, haloaryloxy, phenylamino, pyridinylamino, carboxy, $C_{2-6}$ alkoxycarbonyl and di($C_{1-6}$)alkylaminocarbonyl.

Examples of illustrative substituents on $R^3$ and/or $R^4$ include fluoro, chloro, bromo, cyano, nitro, methyl, hydroxymethyl, trifluoromethyl, pyrazolyl, methylpyrazolyl, dimethylpyrazolyl, propylpyrazolyl, isobutylpyrazolyl, benzylpyrazolyl, morpholinylethyl-pyrazolyl, methylimidazolyl, methylpyridinyl, pyrimidinyl, benzyl, hydroxy, methoxy, ethoxy, difluoromethoxy, trifluoromethoxy, phenoxy, bromophenoxy, benzyloxy, pyridinyloxymethyl, methylenedioxy, difluoromethylenedioxy, methylthio, phenylthio, methylsulphinyl, phenylsulphinyl, methylsulphonyl, phenylsulphonyl, methylsulphonyloxy, amino, methylamino, dimethylamino, phenylamino, N-methyl-N-phenylamino, pyridinylamino, chloropyridinylamino, methylpyridinylamino, dimethylpyridinylamino, methoxypyridinylamino, pyrrolidinyl, morpholinyl, acetylamino, benzofurylcarbonylamino, methoxycarbonylamino, methylsulphonylamino, phenylsulphonylamino, aminomethyl, methylaminomethyl, dimethylaminomethyl, pyridinylaminomethyl, methylpiperazinyl-methyl, morpholinylmethyl, formyl, acetyl, carboxy, methoxycarbonyl, aminocarbonyl, methylaminocarbonyl, (hydroxyethyl)-aminocarbonyl, dimethylaminocarbonyl, N-(hydroxyethyl)-N-methylaminocarbonyl, benzylaminocarbonyl, benzothienylmethyl-aminocarbonyl, azetidinylcarbonyl, pyrrolidinylcarbonyl, piperidinylcarbonyl, methylpiperazinylcarbonyl, morpholinylcarbonyl, aminosulphonyl, methylaminosulphonyl, dimethylaminosulphonyl and tert-butoxycarbonyloxy. Further examples of illustrative substituents on $R^3$ and/or $R^4$ include piperidinylmethylphenyl, triazolyl, N-methyl-N-(methylpiperidinyl) amino and trifluoroacetyl.

Particular examples of illustrative substituents on $R^3$ and/or $R^4$ include bromo, cyano, piperidinylmethylphenyl, triazolyl, methoxy, trifluoromethoxy, bromophenoxy, methylenedioxy, difluoromethylenedioxy, methylsulphonyl, phenylamino, pyridinylamino, N-methyl-N-(methylpiperidinyl)amino, acetyl, trifluoroacetyl, carboxy, methoxycarbonyl and dimethylaminocarbonyl.

Selected examples of illustrative substituents on $R^3$ and/or $R^4$ include bromo, trifluoromethoxy, bromophenoxy, phenylamino, pyridinylamino, carboxy, methoxycarbonyl and dimethylaminocarbonyl.

Selected values of $R^3$ include methyl, phenoxymethyl, bromophenoxymethyl, phenylthiomethyl, aminomethyl, phenylaminomethyl, N-methyl-N-phenylaminomethyl, pyridinylamino-methyl, benzofurylcarbonylaminomethyl, phenylsulphonylaminomethyl, benzothienyl-methylaminocarbonylmethyl, phenyl, benzyl, chlorobenzyl, bromobenzyl, phenylaminobenzyl, pyridinylaminobenzyl, chloropyridinylaminobenzyl, dimethylpyridinylaminobenzyl, methoxypyridinylaminobenzyl, pyrrolidinyl-benzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenyl-methyl, (fluoro)(methyl)biphenylmethyl, dimethylbiphenylmethyl, hydroxymethyl-biphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxy-biphenylmethyl, methylthiobiphenylmethyl, aminobiphenylmethyl, acetylamino-biphenylmethyl, methylsulphonylaminobiphenylmethyl, acetylbiphenylmethyl, aminocarbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, fluoroindolylmethyl, nitroindolylmethyl, methyl-indolylmethyl, hydroxyindolylmethyl, difluoromethoxyindolylmethyl, trifluoromethoxyindolylmethyl, benzyloxyindolylmethyl, difluoromethylenedioxy-indolylmethyl, acetylindolylmethyl, methylsulphonyloxy-indolylmethyl, carboxyindolylmethyl, methoxycarbonyl-indolylmethyl, methylaminocarbonyl-indolylmethyl, (hydroxyethyl) aminocarbonyl-indolylmethyl, dimethylaminocarbonyl-indolylmethyl, N-hydroxyethyl-N-methylaminocarbonyl-indolylmethyl, benzylaminocarbonyl-indolylmethyl, azetidinylcarbonyl-indolylmethyl, piperidinylcarbonyl-indolylmethyl, methylpiperazinylcarbonyl-indolylmethyl, morpholinylcarbonyl-indolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl. Further selected values of $R^3$ include cyanoindolylmethyl, triazolylindolylmethyl, methoxyindolylmethyl, dimethoxyindolyl-methyl, methylenedioxy-indolylmethyl, methylsulphonylindolylmethyl and trifluoroacetylindolylmethyl.

Specific values of $R^3$ include bromophenoxymethyl, bromobenzyl, phenylaminobenzyl, pyridinylaminobenzyl, indolylmethyl, cyanoindolylmethyl, triazolylindolylmethyl, methoxyindolylmethyl, dimethoxyindolylmethyl, trifluoromethoxy-indolylmethyl, methylenedioxy-indolylmethyl, difluoromethylenedioxy-indolylmethyl, methylsulphonylindolylmethyl, acetylindolylmethyl, trifluoroacetyl-indolylmethyl, carboxyindolylmethyl, methoxycarbonyl-indolylmethyl, dimethylaminocarbonyl-indolylmethyl and pyridinylbenzyl.

Particular values of $R^3$ include bromophenoxymethyl, bromobenzyl, phenylaminobenzyl, pyridinylaminobenzyl, indolylmethyl, trifluoromethoxy-indolylmethyl, carboxyindolylmethyl, methoxycarbonyl-indolylmethyl, dimethylaminocarbonyl-indolylmethyl and pyridinylbenzyl.

Typical values of $R^4$ include hydrogen and methyl. In a preferred embodiment, $R^4$ is hydrogen. In another embodiment, $R^4$ is $C_{1-6}$ alkyl, especially methyl.

Alternatively, $R^3$ and $R^4$, when both are attached to the same carbon atom, may together form an optionally substituted Spiro linkage. Thus, $R^3$ and $R^4$, when both are attached to the same carbon atom, may represent, when taken together with the carbon atom to which they are both attached, $C_{3-7}$ cycloalkyl or $C_{3-7}$ heterocycloalkyl, either of which groups may be unsubstituted, or substituted by one or more, typically by one or two, substituents. In this context, $R^3$ and $R^4$, when taken together with the carbon atom to which they are both attached, may suitably represent an optionally substituted cyclopentyl, cyclohexyl, pyrrolidine or piperidine ring.

Alternatively, $R^3$ and $R^4$, when attached to adjacent carbon atoms, may together form an optionally benzo-fused and/or substituted cycloalkyl, phenyl, heterocycloalkyl or heteroaryl (e.g. pyridinyl) ring fused to the morpholine ring. Thus, $R^3$ and $R^4$, when attached to adjacent carbon atoms, may represent, when taken together with the carbon atoms to which they are attached, $C_{5-7}$ cycloalkyl, phenyl, $C_{5-7}$ heterocycloalkyl or heteroaryl (e.g. pyridinyl), any of which groups may be benzo-fused and/or unsubstituted, or substituted by one or more, typically by one or two, substituents. In this context, in one embodiment, $R^3$ and $R^4$, when taken together with the adjacent carbon atoms to which they are attached, suitably represent a phenyl ring fused to the morpholine ring, which phenyl ring may be unsubstituted, or substituted by one or more, typically by one or two, substituents. Also in this context, in another embodiment, $R^3$ and $R^4$, when taken together with the adjacent carbon atoms to which they are attached, suitably represent a benzo-fused cyclopentyl ring, i.e. an indanyl moiety fused to the morpholine ring, which indanyl moiety may be unsubstituted, or substituted by one or more, typically by one or two, substituents.

Examples of suitable substituents on the fused rings referred to in the preceding paragraph include halogen, nitro, hydroxy($C_{1-6}$)alkyl, pyrazolyl, ($C_{1-6}$)alkylpyrazolyl, di($C_{1-6}$)alkyl-pyrazolyl, aryl($C_{1-6}$)alkylpyrazolyl, morpholinyl($C_{1-6}$)alkylpyrazolyl, ($C_{1-6}$)alkylimidazolyl, ($C_{1-6}$)alkylpyridinyl, pyrimidinyl, hydroxy, pyridinyloxy($C_{1-6}$)alkyl, amino, ($C_{1-6}$)alkylpyridinylamino, di($C_{1-6}$)alkylamino($C_{1-6}$)alkyl, pyridinylamino-($C_{1-6}$)alkyl, ($C_{1-6}$)alkylpiperazinyl($C_{1-6}$)alkyl, morpholinyl($C_{1-6}$)alkyl, formyl and $C_{2-6}$ alkoxycarbonyloxy, especially halogen. Further examples include piperidinyl($C_{1-6}$)alkyl-phenyl and N—($C_{1-6}$)alkyl-N—[($C_{1-6}$)alkylpiperidinyl]amino.

Particular examples of such substituents include halogen, piperidinyl($C_{1-6}$)alkyl-phenyl and N—($C_{1-6}$)alkyl-N—[($C_{1-6}$)alkylpiperidinyl]amino.

Selected examples of such substituents include bromo, nitro, hydroxymethyl, pyrazolyl, methylpyrazolyl, dimethylpyrazolyl, propylpyrazolyl, isobutylpyrazolyl, benzylpyrazolyl, morpholinylethylpyrazolyl, methylimidazolyl, methylpyridinyl, pyrimidinyl, hydroxy, pyridinyloxymethyl, amino, methylpyridinylamino, dimethylaminomethyl, pyridinylaminomethyl, methylpiperazinylmethyl, morpholinylmethyl, formyl and tert-butoxycarbonyloxy, especially bromo. Further selected examples include piperidinylmethylphenyl and N-methyl-N-(methylpiperidinyl)-amino.

Specific examples of such substituents include bromo, piperidinylmethylphenyl and N-methyl-N-(methylpiperidinyl) amino.

One sub-class of compounds according to the invention is represented by the compounds of formula (IIA), and pharmaceutically acceptable salts and solvates thereof:

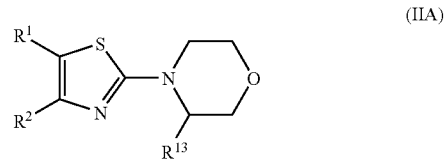

(IIA)

wherein
$R^1$ and $R^2$ are as defined above; and
$R^{13}$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

Where any of the groups in the compounds of formula (IIA) above is stated to be optionally substituted, this group may be unsubstituted, or substituted by one or more substituents. Typically, such groups will be unsubstituted, or substituted by one or two substitutents. Suitably, such groups will be unsubstituted or monosubstituted.

Typically, $R^{13}$ represents $C_{1-6}$ alkyl, aryl($C_{1-6}$)alkyl, aryl($C_{2-6}$)alkynyl, biaryl($C_{1-6}$)alkyl, $C_{3-7}$ heterocycloalkyl($C_{1-6}$)alkyl, $C_{3-7}$ heterocycloalkylcarbonyl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

In a representative embodiment, $R^{13}$ represents $C_{1-6}$ alkyl, aryl($C_{1-6}$)alkyl, biaryl-($C_{1-6}$)alkyl, heteroaryl($C_{1-6}$)alkyl or heteroaryl-aryl($C_{1-6}$)alkyl, any of which groups may be optionally substituted by one or more substituents. Preferably, $R^{13}$ represents methyl, arylmethyl, biarylmethyl, heteroarylmethyl or heteroaryl-arylmethyl, any of which groups may be optionally substituted by one or more substituents.

In a particular embodiment, $R^{13}$ represents substituted or unsubstituted indolyl-($C_{1-6}$)alkyl. Advantageously, $R^{13}$ represents substituted or unsubstituted indolylmethyl.

In a typical embodiment, $R^{13}$ represents substituted or unsubstituted phenyl-($C_{1-6}$)alkyl. Advantageously, $R^{13}$ represents substituted or unsubstituted benzyl.

Illustratively, $R^{13}$ represents methyl, benzyl, phenylethyl, naphthylmethyl, phenylpropynyl, biphenylmethyl, naphthylphenylmethyl, indolinylmethyl, 1,2,3,4-tetrahydroquinolinylmethyl, 1,2,3,4-tetrahydroisoquinolinyl-methyl, piperidinylcarbonyl, 1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, pyrrolo[2,3-b]-pyridinylmethyl, benzimidazolylmethyl, benzotriazolylmethyl, pyridinylmethyl, quinolinylmethyl, isoquinolinylmethyl, benzofurylbenzyl, thienylbenzyl, benzothienylbenzyl, indolylbenzyl, isoxazolylbenzyl, pyrazolylbenzyl, pyridinylbenzyl, pyrimidinylbenzyl or phenylpyridinylmethyl, any of which groups may be optionally substituted by one or more substituents.

Examples of typical substituents on $R^{13}$ include halogen, cyano, nitro, $C_{1-6}$ alkyl, hydroxy($C_{1-6}$)alkyl, trifluoromethyl, pyrazolyl, ($C_{1-6}$)alkylpyrazolyl, di($C_{1-6}$)alkyl-pyrazolyl, aryl($C_{1-6}$)alkylpyrazolyl, morpholinyl($C_{1-6}$)alkylpyrazolyl, ($C_{1-6}$)alkyl-imidazolyl, ($C_{1-6}$)alkylpyridinyl, pyrimidinyl, aryl($C_{1-6}$)alkyl, hydroxy, $C_{1-6}$ alkoxy, difluoromethoxy, trifluoromethoxy, aryloxy, haloaryloxy, aryl($C_{1-6}$)alkoxy, Pyridinyloxy($C_{1-6}$)alkyl, methylenedioxy, difluoromethylenedioxy, $C_{1-6}$ alkylthio, arylthio, $C_{1-6}$ alkylsulphinyl, arylsulphinyl, $C_{1-6}$ alkylsulphonyl, arylsulphonyl, $C_{1-6}$ alkylsulphonyloxy, amino, $C_{1-6}$ alkylamino, di($C_{1-6}$)alkylamino, phenylamino, [($C_{1-6}$)alkyl](phenylamino, pyridinylamino, halopyridinylamino, ($C_{1-6}$)alkylpyridinylamino, di($C_{1-6}$)alkylpyridinylamino, ($C_{1-6}$)alkoxy-pyridinylamino, pyrrolidinyl, morpholinyl, $C_{2-6}$ alkylcarbonylamino, benzofurylcarbonylamino, $C_{2-6}$ alkoxycarbonylamino, $C_{1-6}$ alkylsulphonylamino, arylsulphonylamino, amino($C_{1-6}$)alkyl, ($C_{1-6}$)alkylamino($C_{1-6}$)alkyl, di($C_{1-6}$)alkyl-amino($C_{1-6}$)alkyl, pyridinylamino($C_{1-6}$)alkyl, ($C_{1-6}$)alkylpiperazinyl($C_{1-6}$)alkyl, morpholinyl($C_{1-6}$)alkyl, formyl, $C_{2-6}$ alkylcarbonyl, carboxy, $C_{2-6}$ alkoxycarbonyl, aminocarbonyl, $C_{1-6}$ alkylaminocarbonyl, [hydroxy($C_{1-6}$)alkyl]aminocarbonyl, di($C_{1-6}$)alkylaminocarbonyl, [($C_{1-6}$)alkyl]-[hydroxy($C_{1-6}$)alkyl]aminocarbonyl, aryl($C_{1-6}$)alkylaminocarbonyl, benzothienylmethylaminocarbonyl, azetidinylcarbonyl, pyrrolidinylcarbonyl, piperidinylcarbonyl, ($C_{1-6}$)alkylpiperazinylcarbonyl, morpholinylcarbonyl, aminosulphonyl, $C_{1-6}$ alkylaminosulphonyl, di($C_{1-6}$)alkylaminosulphonyl and $C_{2-6}$ alkoxycarbonyloxy. Further examples of typical substituents on $R^{13}$ include triazolyl and trifluoroacetyl.

Particular examples of typical substituents on $R^{13}$ include halogen, cyano, triazolyl, $C_{1-6}$ alkoxy, trifluoromethoxy, haloaryloxy, methylenedioxy, difluoromethylenedioxy, $C_{1-6}$ alkylsulphonyl, phenylamino, pyridinylamino, $C_{2-6}$ alkylcarbonyl, trifluoroacetyl, carboxy, $C_{2-6}$ alkoxycarbonyl and di($C_{1-6}$)alkylaminocarbonyl.

Selected examples of typical substituents on $R^{13}$ include halogen, trifluoromethoxy, haloaryloxy, phenylamino, pyridinylamino, carboxy, $C_{2-6}$ alkoxycarbonyl and di($C_{1-6}$)alkylaminocarbonyl.

Examples of illustrative substituents on $R^{13}$ include fluoro, chloro, bromo, cyano, nitro, methyl, hydroxymethyl, trifluoromethyl, pyrazolyl, methylpyrazolyl, dimethylpyrazolyl, propylpyrazolyl, isobutylpyrazolyl, benzylpyrazolyl, morpholinylethyl-pyrazolyl, methylimidazolyl, methylpyridinyl, pyrimidinyl, benzyl, hydroxy, methoxy, ethoxy, difluoromethoxy, trifluoromethoxy, phenoxy, bromophenoxy, benzyloxy, pyridinyloxymethyl, methylenedioxy, difluoromethylenedioxy, methylthio, phenylthio, methylsulphinyl, phenylsulphinyl, methylsulphonyl, phenylsulphonyl, methylsulphonyloxy, amino, methylamino, dimethylamino, phenylamino, N-methyl-N-phenylamino, pyridinylamino, chloropyridinylamino, methylpyridinylamino, dimethylpyridinylamino, methoxypyridinylamino, pyrrolidinyl, morpholinyl, acetylamino, benzofurylcarbonylamino, methoxycarbonylamino, methylsulphonylamino, phenylsulphonylamino, aminomethyl, methylaminomethyl, dimethylaminomethyl, pyridinylaminomethyl, methylpiperazinylmethyl, morpholinylmethyl, formyl, acetyl, carboxy, methoxycarbonyl, aminocarbonyl, methylaminocarbonyl, (hydroxyethyl)-aminocarbonyl, dimethylaminocarbonyl, N-(hydroxyethyl)-N-methylaminocarbonyl, benzylaminocarbonyl, benzothienylmethyl-aminocarbonyl, azetidinylcarbonyl, pyrrolidinylcarbonyl, piperidinylcarbonyl, methylpiperazinylcarbonyl, morpholinylcarbonyl, aminosulphonyl, methylamino-sulphonyl, dimethylaminosulphonyl and tert-butoxycarbonyloxy. Further examples of illustrative substituents on $R^{13}$ include triazolyl and trifluoroacetyl.

Particular examples of illustrative substituents on $R^{13}$ include bromo, cyano, triazolyl, methoxy, trifluoromethoxy, bromophenoxy, methylenedioxy, difluoromethylenedioxy, methylsulphonyl, phenylamino, pyridinylamino, acetyl, trifluoroacetyl, carboxy, methoxycarbonyl and dimethylaminocarbonyl.

Selected examples of illustrative substituents on $R^{13}$ include bromo, trifluoromethoxy, bromophenoxy, phenylamino, pyridinylamino, carboxy, methoxycarbonyl and dimethylaminocarbonyl.

Selected values of $R^{13}$ include methyl, phenoxymethyl, bromophenoxymethyl, phenylthiomethyl, aminomethyl, phenylaminomethyl, N-methyl-N-phenylaminomethyl, pyridinylamino-methyl, benzofurylcarbonylaminomethyl, phenylsulphonylaminomethyl, benzothienyl-methylaminocarbonylmethyl, phenyl, benzyl, chlorobenzyl, bromobenzyl, phenylaminobenzyl, pyridinylaminobenzyl, chloropyridinylaminobenzyl, dimethylpyridinylaminobenzyl, methoxypyridinylaminobenzyl, pyrrolidinyl-benzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenylmethyl, (fluoro)(methyl)biphenylmethyl, dimethylbiphenylmethyl, hydroxymethyl-biphenylmethyl, trifluoromethyl-biphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxy-biphenylmethyl, methylthiobiphenylmethyl, aminobiphenylmethyl, acetylamino-biphenylmethyl, methylsulphonylaminobiphenylmethyl, acetylbiphenylmethyl, aminocarbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, fluoroindolylmethyl, nitroindolylmethyl, methyl-indolylmethyl, hydroxyindolylmethyl, difluoromethoxyindolylmethyl, trifluoromethoxyindolylmethyl, benzyloxyindolylmethyl, difluoromethylenedioxy-indolylmethyl, acetylindolylmethyl, methylsulphonyloxy-indolylmethyl, carboxyindolylmethyl, methoxycarbonyl-indolylmethyl, methylaminocarbonyl-indolylmethyl, (hydroxyethyl)aminocarbonyl-indolylmethyl, dimethylaminocarbonyl-indolylmethyl, N-hydroxyethyl-N-methylaminocarbonyl-indolylmethyl, benzylaminocarbonyl-indolylmethyl, azetidinylcarbonyl-indolylmethyl, piperidinylcarbonyl-indolylmethyl, methylpiperazinylcarbonyl-indolylmethyl, morpholinylcarbonyl-indolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl. Further selected values of $R^{13}$ include cyanoindolylmethyl, triazolylindolylmethyl, methoxyindolylmethyl, dimethoxyindolylmethyl, methylenedioxy-indolylmethyl, methylsulphonylindolylmethyl and trifluoroacetylindolylmethyl.

Specific values of $R^{13}$ include bromophenoxymethyl, bromobenzyl, phenylaminobenzyl, pyridinylaminobenzyl, indolylmethyl, cyanoindolylmethyl, triazolylindolylmethyl, methoxyindolylmethyl, dimethoxyindolylmethyl, trifluoromethoxy-indolylmethyl, methylenedioxy-indolylmethyl, difluoromethylenedioxy-indolylmethyl, methylsulphonylindolylmethyl, acetylindolylmethyl, trifluoroacetyl-indolylmethyl, carboxyindolylmethyl, methoxycarbonyl-indolylmethyl, dimethylaminocarbonyl-indolylmethyl and pyridinylbenzyl.

Particular values of $R^{13}$ include bromophenoxymethyl, bromobenzyl, phenylaminobenzyl, pyridinylaminobenzyl, indolylmethyl, trifluoromethoxy-indolylmethyl, carboxyindolylmethyl, methoxycarbonyl-indolylmethyl, dimethylaminocarbonyl-indolylmethyl and pyridinylbenzyl.

One particular sub-group of the compounds of formula (IIA) is represented by the compounds of formula (IIB), and pharmaceutically acceptable salts and solvates thereof:

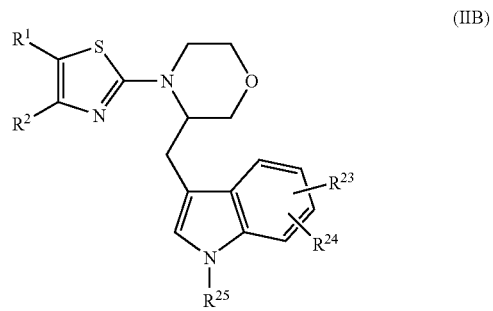

wherein
$R^1$ and $R^2$ are as defined above;
$R^{23}$ represents hydrogen, halogen, cyano, nitro, $C_{1-6}$ alkyl, hydroxy($C_{1-6}$)alkyl, trifluoromethyl, aryl($C_{1-6}$)alkyl, triazolyl, hydroxy, $C_{1-6}$ alkoxy, difluoromethoxy, trifluoromethoxy, aryloxy, aryl($C_{1-6}$)alkoxy, $C_{1-6}$ alkylthio, $C_{1-6}$ alkylsulphinyl, arylsulphinyl, $C_{1-6}$ alkylsulphonyl, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl, trifluoroacetyl, carboxy, $C_{2-6}$ alkoxycarbonyl, aminocarbonyl, $C_{1-6}$ alkylaminocarbonyl, [hydroxy-($C_{1-6}$)alkyl]aminocarbonyl, di($C_{1-6}$)alkylaminocarbonyl, [($C_{1-6}$)alkyl][hydroxy-($C_{1-6}$)alkyl]aminocarbonyl, aryl($C_{1-6}$)alkylaminocarbonyl, azetidinylcarbonyl, pyrrolidinylcarbonyl, piperidinylcarbonyl, ($C_{1-6}$)alkylpiperazinylcarbonyl or morpholinylcarbonyl; and
$R^{24}$ represents hydrogen, halogen, $C_{1-6}$ alkoxy or di($C_{1-6}$)alkylaminocarbonyl; or
$R^{23}$ and $R^{24}$, when situated on adjacent carbon atoms, together represent methylenedioxy or difluoromethylenedioxy; and
$R^{25}$ represents hydrogen or $C_{1-6}$ alkyl.

The present invention also provides a compound of formula (IIB) as depicted above, or a pharmaceutically acceptable salt or solvate thereof, wherein
$R^1$ and $R^2$ are as defined above;
$R^{23}$ represents hydrogen, halogen, cyano, nitro, $C_{1-6}$ alkyl, hydroxy($C_{1-6}$)alkyl, trifluoromethyl, aryl($C_{1-6}$)alkyl, hydroxy, $C_{1-6}$ alkoxy, difluoromethoxy, trifluoromethoxy, aryloxy, aryl($C_{1-6}$)alkoxy, $C_{1-6}$ alkylthio, $C_{1-6}$ alkylsulphinyl, arylsulphinyl, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl, carboxy, $C_{2-6}$ alkoxycarbonyl, aminocarbonyl, $C_{1-6}$ alkylaminocarbonyl, [hydroxy($C_{1-6}$)alkyl]aminocarbonyl, di($C_{1-6}$)alkylaminocarbonyl, [($C_{1-6}$)alkyl][hydroxy-($C_{1-6}$)alkyl]aminocarbonyl, aryl($C_{1-6}$)alkylaminocarbonyl, azetidinylcarbonyl, pyrrolidinylcarbonyl, piperidinylcarbonyl, ($C_{1-6}$)alkylpiperazinylcarbonyl or morpholinylcarbonyl; and
$R^{24}$ and $R^{25}$ represent hydrogen.

Particular values of $R^{23}$ include hydrogen, cyano, triazolyl, $C_{1-6}$ alkoxy, trifluoromethoxy, $C_{1-6}$ alkylsulphonyl, $C_{2-6}$ alkylcarbonyl, trifluoroacetyl, carboxy, $C_{2-6}$ alkoxycarbonyl and di($C_{1-6}$)alkylaminocarbonyl.

Typical values of $R^{23}$ include hydrogen, trifluoromethoxy, carboxy, $C_{2-6}$ alkoxycarbonyl and di($C_{1-6}$)alkylaminocarbonyl.

Representative values of $R^{23}$ include hydrogen, fluoro, chloro, bromo, cyano, nitro, methyl, hydroxymethyl, trifluoromethyl, benzyl, triazolyl, hydroxy, methoxy, ethoxy, difluoromethoxy, trifluoromethoxy, phenoxy, benzyloxy, methylthio, methylsulphinyl, methylsulphonyl, phenylsulphinyl, phenylsulphonyl, methylsulphonyloxy, amino, acetylamino, methylsulphonylamino, acetyl, trifluoroacetyl, carboxy, methoxycarbonyl, aminocarbonyl, methylaminocarbonyl, (hydroxyethyl)aminocarbonyl, dimethylaminocarbonyl, N-(hydroxyethyl)-N-methylaminocarbonyl, benzylaminocarbonyl, azetidinylcarbonyl, pyrrolidinylcarbonyl, piperidinylcarbonyl, methylpiperazinylcarbonyl and morpholinylcarbonyl.

Illustrative values of $R^{23}$ include hydrogen, fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylthio, methylsulphinyl, phenylsulphinyl, phenylsulphonyl, methylsulphonyloxy, amino, acetylamino, methylsulphonylamino, acetyl, carboxy, methoxycarbonyl, aminocarbonyl, methylaminocarbonyl, (hydroxyethyl)aminocarbonyl, dimethylaminocarbonyl, N-(hydroxyethyl)-N-methylaminocarbonyl, benzylaminocarbonyl, azetidinylcarbonyl, pyrrolidinylcarbonyl, piperidinylcarbonyl, methylpiperazinylcarbonyl and morpholinylcarbonyl.

Specific values of $R^{23}$ include hydrogen, cyano, triazolyl, methoxy, trifluoromethoxy, methylsulphonyl, acetyl, trifluoroacetyl, carboxy, methoxycarbonyl and dimethylaminocarbonyl.

Selected values of $R^{23}$ include hydrogen, trifluoromethoxy, carboxy, methoxycarbonyl and dimethylaminocarbonyl.

Suitably, $R^{24}$ represents hydrogen or $C_{1-6}$ alkoxy. In a particular embodiment, $R^{24}$ represents hydrogen. In another embodiment, $R^{24}$ represents halogen, especially chloro. In a further embodiment, $R^{24}$ represents $C_{1-6}$ alkoxy, especially methoxy. In an additional embodiment, $R^{24}$ represents di($C_{1-6}$)alkylaminocarbonyl, especially dimethylaminocarbonyl.

In a particular embodiment, $R^{25}$ represents hydrogen. In another embodiment, $R^{24}$ represents $C_{1-6}$ alkyl, especially methyl.

Another particular sub-group of the compounds of formula (IIA) is represented by the compounds of formula (IIC), and pharmaceutically acceptable salts and solvates thereof:

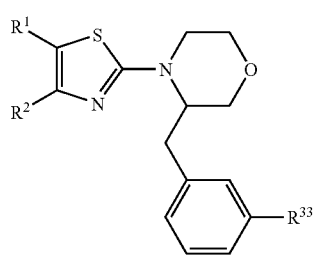

(IIC)

wherein
$R^1$ and $R^2$ are as defined above;
$R^{33}$ represents halogen or —$NHR^{34}$; or aryl or heteroaryl, either of which groups may be optionally substituted by one or more substituents; and
$R^{34}$ represents phenyl, pyridinyl, halopyridinyl, ($C_{1-6}$) alkylpyridinyl, di($C_{1-6}$)alkylpyridinyl or ($C_{1-6}$)alkoxypyridinyl.

Suitably, $R^{33}$ represents halogen or —$NHR^{34}$, in which $R^{34}$ is as defined above. In one embodiment, $R^{33}$ represents halogen, especially bromo. In another embodiment, $R^{33}$ represents —$NHR^{34}$, in which $R^{34}$ is as defined above.

In one embodiment, $R^{33}$ represents unsubstituted or substituted aryl. In another embodiment, $R^{33}$ represents unsubstituted or substituted heteroaryl.

Suitable values of $R^{34}$ include phenyl, pyridinyl, chloropyridinyl, methylpyridinyl, dimethylpyridinyl or methoxypyridinyl. Particular values of $R^{34}$ include phenyl and pyridinyl.

Illustratively, $R^{33}$ represents halogen or —$NHR^{34}$, in which $R^{34}$ is as defined above. Additionally, $R^{33}$ represents phenyl, naphthyl, benzofuryl, thienyl, benzothienyl, indolyl, isoxazolyl, pyrazolyl, pyridinyl or pyrimidinyl, any of which groups may be optionally substituted by one or more substituents.

Selected examples of suitable substituents on $R^{33}$ include halogen, cyano, $C_{1-6}$ alkyl, hydroxy($C_{1-6}$)alkyl, trifluoromethyl, $C_{1-6}$ alkoxy, trifluoromethoxy, aryloxy, methylenedioxy, $C_{1-6}$ alkylthio, arylsulphonyl, amino, $C_{2-6}$ alkylcarbonylamino, $C_{1-6}$ alkylsulphonylamino, $C_{2-6}$ alkylcarbonyl and aminocarbonyl.

Selected examples of representative substituents on $R^{33}$ include fluoro, chloro, bromo, cyano, methyl, hydroxymethyl, trifluoromethyl, methoxy, ethoxy, trifluoromethoxy, phenoxy, methylenedioxy, methylthio, phenylsulphonyl, amino, acetylamino, methylsulphonylamino, acetyl and aminocarbonyl.

Specific values of $R^{33}$ include bromo, phenylamino, pyridinylamino, chloropyridinylamino, methylpyridinylamino, dimethylpyridinylamino, methoxypyridinylamino, phenyl, fluorophenyl, difluorophenyl, chlorophenyl, dichlorophenyl, bromophenyl, cyanophenyl, methylphenyl, (fluoro)(methyl)phenyl, dimethylphenyl, hydroxymethylphenyl, trifluoromethylphenyl, bis(trifluoromethyl)phenyl, methoxyphenyl, dimethoxyphenyl, ethoxyphenyl, methylenedioxyphenyl, trifluoromethoxyphenyl, phenoxyphenyl, methylthiophenyl, aminophenyl, acetylaminophenyl, methylsulphonylaminophenyl, acetylphenyl, aminocarbonylphenyl, naphthyl, benzofuryl, thienyl, methylthienyl, acetylthienyl, benzothienyl, phenylsulphonylindolyl, dimethylisoxazolyl, methylpyrazolyl, benzylpyrazolyl, pyridinyl, fluoropyridinyl, chloropyridinyl, methoxypyridinyl and pyrimidinylbenzyl.

Particular values of $R^{33}$ include bromo, phenylamino, pyridinylamino and pyridinyl.

Other sub-classes of compounds according to the invention are represented by the compounds of formula (IID-1) and (IID-2), and pharmaceutically acceptable salts and solvates thereof:

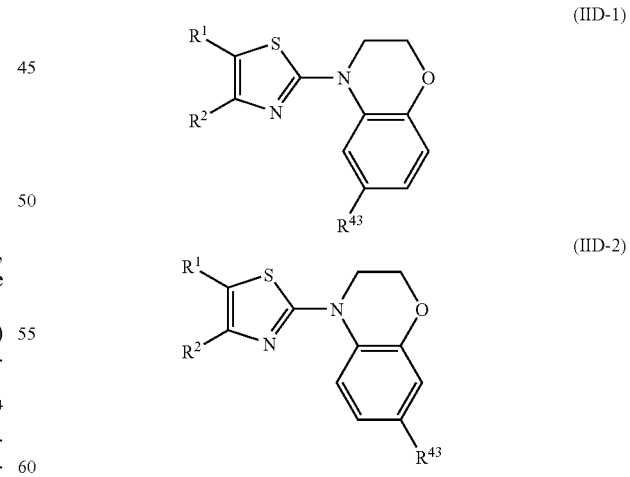

wherein
$R^1$ and $R^2$ are as defined above; and
$R^{43}$ represents hydrogen, halogen, nitro, hydroxy($C_{1-6}$) alkyl, piperidinyl($C_{1-6}$)alkylphenyl, pyrazolyl, ($C_{1-6}$)alkylpyrazolyl, di($C_{1-6}$)alkylpyrazolyl, aryl($C_{1-6}$)alkylpyrazolyl, morpholinyl($C_{1-6}$)alkylpyrazolyl, imidazolyl, ($C_{1-6}$)alkylimidazolyl, pyridinyl, $(C_{1-6})$alkylpyridinyl, pyrimidinyl, hydroxy, pyridinyloxy$(C_{1-6})$alkyl, amino, pyridinylamino, halopyridinylamino, $(C_{1-6})$alkylpyridinylamino, di$(C_{1-6})$alkylpyridinylamino, $(C_{1-6})$alkoxypyridinylamino, N—$(C_{1-6})$alkyl-N—[$(C_{1-6})$alkylpiperidinyl]amino, amino$(C_{1-6})$alkyl, $(C_{1-6})$alkylamino$(C_{1-6})$alkyl, di$(C_{1-6})$alkylamino$(C_{1-6})$alkyl, pyridinylamino$(C_{1-6})$alkyl, $(C_{1-6})$alkylpiperazinyl$(C_{1-6})$alkyl, morpholinyl$(C_{1-6})$alkyl, formyl or $C_{2-6}$ alkoxycarbonyloxy.

Typically, $R^{43}$ represents hydrogen, halogen, nitro, hydroxy$(C_{1-6})$alkyl, pyrazolyl, $(C_{1-6})$alkylpyrazolyl, di$(C_{1-6})$alkylpyrazolyl, aryl$(C_{1-6})$alkylpyrazolyl, morpholinyl-$(C_{1-6})$alkylpyrazolyl, imidazolyl, $(C_{1-6})$alkylimidazolyl, pyridinyl, $(C_{1-6})$alkylpyridinyl, pyrimidinyl, hydroxy, pyridinyloxy$(C_{1-6})$alkyl, amino, pyridinylamino, halopyridinylamino, $(C_{1-6})$alkylpyridinylamino, di$(C_{1-6})$alkylpyridinylamino, $(C_{1-6})$alkoxypyridinylamino, amino$(C_{1-6})$alkyl, $(C_{1-6})$alkylamino$(C_{1-6})$alkyl, di$(C_{1-6})$alkylamino-$(C_{1-6})$alkyl, pyridinylamino$(C_{1-6})$alkyl, $(C_{1-6})$alkylpiperazinyl$(C_{1-6})$alkyl, morpholinyl-$(C_{1-6})$alkyl, formyl or $C_{2-6}$ alkoxycarbonyloxy.

Particular values of $R^{43}$ include halogen, piperidinyl$(C_{1-6})$alkylphenyl and N—$(C_{1-6})$alkyl-N—[$(C_{1-6})$alkylpiperidinyl]amino.

Suitably, $R^{43}$ represents halogen.

Specific values of $R^{43}$ include bromo, nitro, hydroxymethyl, pyrazolyl, methylpyrazolyl, dimethylpyrazolyl, propylpyrazolyl, isobutylpyrazolyl, benzylpyrazolyl, morpholinylethylpyrazolyl, methylimidazolyl, methylpyridinyl, pyrimidinyl, hydroxy, pyridinyloxymethyl, amino, methylpyridinylamino, dimethylaminomethyl, pyridinylaminomethyl, methylpiperazinylmethyl, morpholinylmethyl, formyl and tert-butoxycarbonyloxy, especially bromo.

Definitive values of $R^{43}$ include bromo, piperidinylmethylphenyl and N-methyl-N-(methylpiperidinyl)amino, especially bromo.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

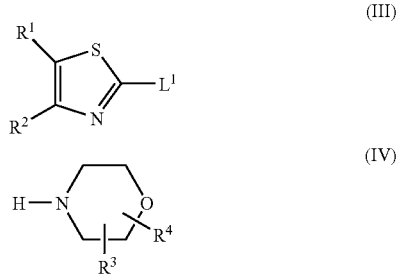

wherein $R^1$, $R^2$, $R^3$ and $R^4$ are as defined above, and $L^1$ represents a suitable leaving group.

The leaving group $L^1$ is typically a halogen atom, e.g. bromo or chloro.

The reaction is conveniently effected at an elevated temperature in a suitable solvent, e.g. a lower alkanol such as isopropanol or a cyclic ether such as tetrahydrofuran, typically under basic conditions, e.g. in the presence of an organic base such as N,N-diisopropylethylamine.

Alternatively, the reaction may be effected at an elevated temperature in a solvent such as 2-ethoxyethanol in the presence of a catalytic quantity of a mineral acid, e.g. concentrated hydrochloric acid.

In another alternative, the reaction may be effected at an elevated temperature in a suitable solvent, e.g. a cyclic ether such as tetrahydrofuran, typically under basic conditions, e.g. in the presence of an inorganic base such as sodium tert-butoxide, in the presence of a transition metal catalyst. The transition metal catalyst is suitably palladium(II) acetate, in which case the reaction will ideally be performed in the presence of tert-butylphosphonium tetrafluoroborate.

The intermediates of formula (III) above wherein $L^1$ is bromo may be prepared from a compound of formula (V):

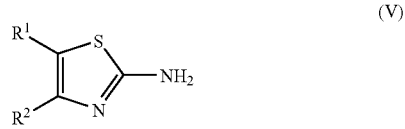

wherein $R^1$ and $R^2$ are as defined above; by diazotization/bromination.

The reaction is conveniently effected by stirring compound (V) with tert-butyl nitrite and copper(II) bromide in a suitable solvent, e.g. acetonitrile.

The intermediates of formula (V) above may be prepared by reacting thiourea with a compound of formula (VI):

wherein $R^1$ and $R^2$ are as defined above, and $L^2$ represents a suitable leaving group.

The leaving group $L^2$ is typically a halogen atom, e.g. bromo or chloro.

The reaction is conveniently effected at an elevated temperature in a suitable solvent, e.g. a cyclic ether such as tetrahydrofuran, typically under basic conditions, e.g. in the presence of an organic base such as N,N-diisopropylethylamine or 2,6-lutidine, or an inorganic base such as sodium carbonate.

Alternatively, the reaction may be accomplished by heating the reactants in a lower alkanol solvent, e.g. a $C_{1-6}$ alkyl alcohol such as ethanol.

In another procedure, the compounds of formula (I) may be prepared by a process which comprises reacting a compound of formula (VI) as defined above with a compound of formula (VII):

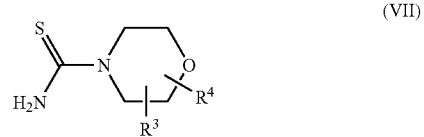

wherein $R^3$ and $R^4$ are as defined above; under conditions analogous to those described above for the reaction between thiourea and compound (VI).

Where they are not commercially available, the starting materials of formula (IV), (VI) and (VII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein $R^3$ represents aryl($C_{1-6}$)alkyl, substituted on the aryl moiety by a halogen atom such as bromo, may be converted into the corresponding compound wherein $R^3$ represents biaryl($C_{1-6}$) alkyl or heteroaryl-aryl($C_{1-6}$)alkyl by treatment with, respectively, an aryl or heteroaryl boronic acid, in the presence of a catalyst. Similarly, a compound of formula (I) wherein $R^3$ represents heteroaryl-($C_{1-6}$)alkyl, substituted on the heteroaryl moiety by a halogen atom such as bromo, may be converted into the corresponding compound wherein $R^3$ represents aryl-heteroaryl-($C_{1-6}$)alkyl by treatment with an aryl boronic acid, in the presence of a catalyst. The catalyst may typically be a transition metal catalyst. A suitable catalyst is [1,1'-bis(diphenylphosphino)ferrocene]dichloropalladium (II) or tetrakis(triphenylphosphine)-palladium(0), in which case the transformation may conveniently be effected at an elevated temperature in the presence of a base such as caesium carbonate, sodium carbonate or potassium carbonate, in an inert solvent such as 1,2-dimethoxyethane or 1,4-dioxane. Alternatively, the catalyst may be palladium(II) acetate, in which case the transformation may conveniently be effected at an elevated temperature in the presence of 2-dicyclohexylphosphino-2',6'-dimethoxybiphenyl and potassium phosphate.

A compound of formula (I) wherein $R^3$ represents hydroxymethyl may be converted into the corresponding compound wherein $R^3$ represents a substituted aminomethyl moiety, e.g. phenylaminomethyl, N-methyl-N-phenylaminomethyl, pyridin-3-ylaminomethyl, indolin-1-ylmethyl, 1,2,3,4-tetrahydroquinolin-1-ylmethyl or 1,2,3,4-tetrahydroisoquinolin-2-ylmethyl, by a two-stage procedure which comprises (i) Swern oxidation of the hydroxymethyl derivative by treatment with oxalyl chloride and dimethyl sulphoxide followed by triethylamine; and (ii) reductive amination of the formyl derivative thereby obtained by treatment with the appropriate amine, e.g. aniline, N-methylaniline, 3-aminopyridine, indoline, 1,2,3,4-tetrahydroquinoline or 1,2,3,4-tetrahydroisoquinoline, in the presence of a reducing agent such as sodium cyanoborohydride.

A compound of formula (I) wherein $R^3$ represents hydroxymethyl may be converted into the corresponding compound wherein $R^3$ represents an optionally substituted $C_{3-7}$ heterocycloalkylcarbonyl moiety, e.g. piperidin-1-ylcarbonyl, 1,2,3,4-tetrahydroquinolin-1-ylcarbonyl, 6-methyl-1,2,3,4-tetrahydroquinolin-1-ylcarbonyl, 6-methoxy-1,2,3,4-tetrahydroquinolin-1-ylcarbonyl, 1,2,3,4-tetrahydroisoquinolin-2-ylcarbonyl or 1,2,3,4-tetrahydroquinoxalin-1-ylcarbonyl, by a two-stage procedure which comprises (i) oxidation of the hydroxymethyl moiety by treatment with potassium permanganate; and (ii) reaction of the carboxy derivative thereby obtained with the appropriate amine, e.g. piperidine, 1,2,3,4-tetrahydroquinoline, 6-methyl-1,2,3,4-tetrahydroquinoline, 6-methoxy-1,2,3,4-tetrahydroquinoline, 1,2,3,4-tetrahydro-isoquinoline or 1,2,3,4-tetrahydroquinoxaline, in the presence of a condensing agent such as 1-(3-dimethylaminopropyl)-3-ethylcarbodiimide, or O-(benzotriazol-1-yl)-N,N,N',N'-tetramethyluronium hexafluorophosphate (HBTU).

A compound of formula (I) wherein $R^3$ contains a phenyl moiety substituted by chloro may be converted into the corresponding compound wherein the phenyl ring is substituted by morpholin-4-yl by treatment with morpholine in the presence of tris(dibenzylideneacetone)dipalladium(0), 2-(di-tert-butylphosphino)biphenyl and sodium tert-butoxide. A compound of formula (I) wherein $R^3$ contains a phenyl moiety substituted by bromo may be converted into the corresponding compound wherein the phenyl ring is substituted by pyrrolidin-1-yl by treatment with pyrrolidine in the presence of tris(dibenzylideneacetone)dipalladium(0), 2-dicyclohexylphosphino-2',4',6'-triisopropyl-1,1'-biphenyl and a base such as potassium carbonate. Similarly, a compound of formula (I) wherein $R^3$ contains a phenyl moiety substituted by bromo may be converted into the corresponding compound wherein the phenyl ring is substituted by an amino moiety (e.g. a group of formula —$NHR^{34}$ as defined above) by treatment with the appropriate amine (e.g. a compound of formula $H_2N—R^{34}$ such as aniline or 4-aminopyridine) in the presence of tris(dibenzylideneacetone)dipalladium(0), 2-(dicyclohexylphosphino)-2',4',6'-tri-isopropyl-1,1'-biphenyl (X-Phos) and a base such as sodium tert-butoxide.

A compound of formula (I) wherein $R^3$ contains an indole moiety may be methylated on the indole ring by treatment with a methyl halide, e.g. iodomethane, in the presence of a strong base such as sodium hydride. A compound of formula (I) wherein $R^3$ contains an indole moiety may be acetylated on the indole ring by treatment with acetic anhydride and 4-dimethylamino-pyridine, typically in the presence of an organic base such as triethylamine. A compound of formula (I) wherein $R^3$ contains an indoline moiety may be converted into the corresponding compound wherein $R^3$ contains an indole moiety by treatment with an oxidising agent such as manganese dioxide. A compound of formula (I) wherein $R^3$ contains a hydroxy substituent may be converted into the corresponding compound wherein $R^3$ contains a $C_{1-6}$ alkylsulphonyloxy substituent, e.g. methylsulphonyloxy, by treatment with a $C_{1-6}$ alkylsulphonyl halide, e.g. methanesulphonyl chloride. A compound of formula (I) wherein $R^3$ contains an amino (—$NH_2$) or carboxy (—$O_2H$) moiety may be converted into the corresponding compound wherein $R^3$ contains an amido moiety (—NHCO— or —CONH— respectively) by treatment with, respectively, a compound containing a carboxy or amino group, in the presence of O-(benzotriazol-1-yl)-N,N,N',N'-tetramethyluronium hexafluorophosphate (HBTU), typically in a dipolar aprotic solvent such as N,N-dimethylformamide. A compound of formula (I) wherein $R^3$ contains an amino substituent may be converted into the corresponding compound wherein $R^3$ contains an arylsulphonylamino substituent, e.g. phenylsulphonylamino, by treatment with an arylsulphonyl halide, e.g. benzenesulphonyl chloride.

A compound of formula (I) wherein $R^3$ contains a $C_{2-6}$ alkoxycarbonyl substituent, e.g. methoxycarbonyl, may be converted into the corresponding compound wherein $R^3$ contains a carboxy (—$CO_2H$) substituent under standard saponification conditions, e.g. by treatment with a base such as lithium hydroxide. A compound of formula (I) wherein $R^3$ contains a carboxy (—$CO_2H$) substituent may be converted into the corresponding compound wherein $R^3$ contains an amido substituent, e.g. methylaminocarbonyl, 2-hydroxyethylaminocarbonyl, dimethylaminocarbonyl, N-(2-hydroxyethyl)-N-methylaminocarbonyl, benzylaminocarbonyl, azetidin-1-ylcarbonyl, pyrrolidin-1-ylcarbonyl, piperidin-1-ylcarbonyl, 4-methylpiperazin-1-ylcarbonyl or morpholin-4-ylcarbonyl, by a two-stage procedure which comprises (i) treatment of the carboxy derivative with pentafluorophenol in the presence of a condensing agent such as 1-(3-dimethylaminopropyl)-3-ethylcarbodiimide; and (ii) reaction of the pentafluorophenyl ester thereby obtained with the appropriate amine, e.g. methylamine, 2-hydroxy-ethylamine, dimethylamine, N-(2-hydroxyethyl)-N-methylamine, benzylamine, azetidine, pyrrolidine, piperidine, 1-methylpiperazine or morpholine.

A compound of formula (I) wherein $R^3/R^4$ contains a nitro moiety may be converted into the corresponding compound wherein $R^3/R^4$ contains an amino (—$NH_2$) moiety by catalytic hydrogenation, typically by treatment with hydrogen in the presence of a hydrogenation catalyst, e.g. palladium on charcoal. A compound of formula (I) wherein $R^3/R^4$ contains an amino (—$NH_2$) moiety may be converted into the corresponding compound wherein $R^3/R^4$ contains a heteroarylamino moiety, e.g. 6-methylpyridin-3-ylamino, by treatment with the appropriate heteroaryl halide, e.g. 5-bromo-2-methylpyridine, in the presence of palladium(II) acetate, 2-bis(dicyclohexylphosphino)-biphenyl and a base such as sodium tert-butoxide.

A compound of formula (I) wherein $R^3/R^4$ contains a benzo moiety substituted by a halogen atom, e.g. bromo, may be converted into the corresponding compound wherein $R^3/R^4$ contains a benzo moiety substituted by an aryl or heteroaryl group, e.g. piperidinyl-methylphenyl, pyrazol-3-yl, 1-methylpyrazol-4-yl, 1-propylpyrazol-4-yl, 1-isobutyl-pyrazol-4-yl, 1-benzylpyrazol-4-yl, 1-[2-(morpholin-4-yl)ethyl]pyrazol-4-yl, 6-methyl-pyridin-3-yl or pyrimidin-5-yl, by treatment with the appropriate aryl or heteroaryl boronic acid or a cyclic ester thereof formed with an organic diol, e.g. pinacol, in the presence of a catalyst. Similarly, a compound of formula (I) wherein $R^3/R^4$ contains a benzo moiety substituted by a boronic acid [—$B(OH)_2$] moiety may be converted into the corresponding compound wherein $R^3/R^4$ contains a benzo moiety substituted by a heteroaryl group, e.g. methylimidazolyl, by treatment with the appropriate heteroaryl halide, e.g. bromide, derivative in the presence of a catalyst. The catalyst may typically be a transition metal catalyst. A suitable catalyst is tetrakis(triphenylphosphine)palladium (0), in which case the transformation may conveniently be effected at an elevated temperature in the presence of a base such as sodium carbonate, potassium carbonate or potassium phosphate, optionally in the presence of tetrabutylammonium bromide.

A compound of formula (I) wherein $R^3/R^4$ contains a benzo moiety substituted by a halogen atom, e.g. bromo, may be converted into the corresponding compound wherein $R^3/R^4$ contains a benzo moiety substituted by a formyl (—CHO) group by treatment with a strong base, e.g. n-butyllithium, and N,N-dimethylformamide. A compound of formula (I) wherein $R^3/R^4$ contains a benzo moiety substituted by a formyl (—CHO) group may be converted into the corresponding compound wherein $R^3/R^4$ contains a benzo moiety substituted by hydroxymethyl by treatment with a reducing agent such as sodium borohydride. A compound of formula (I) wherein $R^3/R^4$ contains a benzo moiety substituted by a formyl (—CHO) group may be converted into the corresponding compound wherein $R^3/R^4$ contains a benzo moiety substituted by an aminomethyl moiety (e.g. dimethylaminomethyl, pyridin-3-ylaminomethyl, 4-methylpiperazin-1-ylmethyl or morpholin-4-ylmethyl) by treatment with the appropriate amine (e.g. dimethylamine, pyridin-3-ylamine, 1-methylpiperazine or morpholine) and a reducing agent which typically consists of a mixture of phenylsilane and dibutyltin dichloride. A compound of formula (I) wherein $R^3/R^4$ contains a benzo moiety substituted by a $C_{2-6}$ alkoxycarbonyloxy group, e.g. tert-butoxycarbonyloxy, may be converted into the corresponding compound wherein $R^3/R^4$ contains a benzo moiety substituted by hydroxy under standard hydrolytic conditions, e.g. by treatment with trifluoroacetic acid.

A compound of formula (I) wherein $R^3/R^4$ contains a benzo moiety substituted by a halogen atom, e.g. bromo, may be converted into the corresponding compound wherein $R^3/R^4$ contains a benzo moiety substituted by an amino moiety, e.g. ($C_{1-6}$)alkylpiperidinylamino or N—($C_{1-6}$)alkyl-N—[($C_{1-6}$)alkylpiperidinyl]amino, by treatment with the appropriate amine, e.g. 4-amino-1-methylpiperidine or 1-methyl-4-(methylamino)piperidine, in the presence of a catalyst. The catalyst may typically be a transition metal catalyst. A suitable catalyst is tris(dibenzylideneacetone)dipalladium(0), in which case the transformation may conveniently be effected at an elevated temperature in the presence of 1,2,3,4,5-pentaphenyl-1'-(di-tert-butylphosphino)ferrocene and a base such as sodium tert-butoxide. Alternatively, the catalyst may be di-μ-bromobis(tri-tert-butylphosphino)dipalladium(I), in which case the transformation may conveniently be effected at an elevated temperature in the presence of a base such as sodium tert-butoxide.

A compound of formula (I) wherein $R^3/R^4$ contains a benzo moiety substituted by a NH functionality may be converted into the corresponding compound wherein $R^3/R^4$ contains a benzo moiety substituted by a N-methyl functionality by treatment with formaldehyde in the presence of a reducing agent such as sodium triacetoxyborohydride.

A compound of formula (I) wherein $R^1$ represents —$CO_2H$ may be converted into the corresponding compound wherein $R^3$ represents —$CONR^bR^c$ by treatment with an amine of formula H—$NR^bR^c$ in the presence of 1-(3-dimethylaminopropyl)-3-ethylcarbodiimide hydrochloride (EDC) and 1-hydroxybenzotriazole hydrate.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 μM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the $IC_{50}$.

When tested in the above assay, the compounds of the accompanying Examples were all found to possess $IC_{50}$ values for inhibition of activity of human PI3Kα and/or PI3Kβ and/or PI3Kγ and/or PI3Kδ of 50 μM or better.

EXAMPLES

Abbreviations

DCM: dichloromethane
DMF: N,N-dimethylformamide
DME: ethylene glycol dimethyl ether
DMSO: dimethylsulphoxide;
$Et_2O$: diethyl ether
THF: tetrahydrofuran
r.t.: room temperature
sat.: saturated
EtOAc: ethyl acetate
MeOH: methanol
IPA: isopropyl alcohol
RT: retention time
Me: methyl
h: hour
conc.: concentrated
cat.: catalytic
MeCN: acetonitrile
$SiO_2$: silica
br.: broad
w or wt: weight
M: mass
$^tBu$: tert-butyl
v: volume
BuOH: butanol
NBS: N-bromosuccinimide
DIPEA: N,N-diisopropylethylamine
brine: saturated aqueous sodium chloride solution
HPLC: High Performance Liquid Chromatography
LCMS: Liquid Chromatography Mass Spectrometry
ES+: Electrospray Positive Ionisation
EDC: 1-(3-dimethylaminopropyl)-3-ethylcarbodiimide hydrochloride
DMPU: 1,3-dimethyl-3,4,5,6-tetrahydro-2(1H)-pyrimidinone
$Pd_2dba_3$: tris(dibenzylideneacetone)dipalladium(0)
X-Phos: 2-(dicyclohexylphosphino)-2',4',6'-tri-isopropyl-1,1'-biphenyl Analytical Conditions All NMRs were obtained either at 300 MHz or 400 MHz.

Compounds were named with the aid of ACD Labs Name (v. 7.0 or 9.0) supplied by Advanced Chemical Development, Toronto, Canada.

All reactions involving air- or moisture-sensitive reagents were performed under a nitrogen atmosphere using dried solvents and glassware.

All compound purities and retention times were determined by LCMS using one of Methods 1-6 below.

All compounds that required preparative HPLC were purified using one of Methods 7-9 below.

Method 1: Luna C18(2) 100×4.6 mm, 5 μm column. Mobile phase A: 99.92% water, 0.08% formic acid. Mobile phase B: 99.92% MeCN, 0.08% formic acid.

Gradient program (flow rate 3.0 mL/min, column temperature 35° C.):

| Time | A % | B % |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Method 2: Gemini C18 50×4.6 mm, 5 μm column. Mobile phase A: 99.9% 10 mM ammonium formate, 0.1% formic acid. Mobile phase B: 94.9% MeCN, 0.1% formic acid, 5% mobile phase A.

Gradient program (flow rate 0.9 mL/min, column temperature 40° C.):

| Time | A % | B % |
|---|---|---|
| 0.00 | 95.0 | 5.0 |
| 2.00 | 5.0 | 95.0 |
| 5.50 | 5.0 | 95.0 |

Method 3: Gemini C18 50×4.6 mm, 5 μm column. Mobile phase A: 99.9% 10 mM ammonium formate, 0.1% ammonia. Mobile phase B: 94.9% MeCN, 0.1% ammonia, 5% mobile phase A.

Gradient program (flow rate 3.0 mL/min, column temperature 40° C.):

| Time | A % | B % |
|---|---|---|
| 0.00 | 95.0 | 5.0 |
| 2.00 | 5.0 | 95.0 |
| 5.50 | 5.0 | 95.0 |

Method 4: Gemini C18 50×4.6 mm, 5 μm column. Mobile phase A: 99.9% ammonium formate, 0.1% formic acid. Mobile phase B: 94.9% MeCN, 0.1% formic acid, 5% mobile phase A.

Gradient program (flow rate 0.9 mL/min, column temperature 40° C.):

| Time | A % | B % |
|---|---|---|
| 0.00 | 95.0 | 5.0 |
| 2.00 | 5.0 | 95.0 |
| 4.00 | 5.0 | 95.0 |

Method 5: Luna C18(2) 100×4.6 mm, 5 μm column. Mobile phase A: 99.92% water, 0.08% formic acid. Mobile phase B: 99.92% MeCN, 0.08% formic acid.

Gradient program (flow rate 3.0 mL/min, column temperature 35° C.):

| Time | A % | B % |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Method 6: Luna C18(2) 100×4.6 mm, 5 μm column. Mobile phase A: 5 mM NH$_4$OAc, pH 5.8. Mobile phase B: 95:5 MeCN: 100 mM NH$_4$OAc, pH 5.8.

Gradient program (flow rate 3.0 mL/min, column temperature 35° C.):

| Time | A % | B % |
|------|-----|-----|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Method 7: Luna C18(2) 250×21.2 mm, 5 μm column. Mobile phase A: 99.92% water, 0.08% formic acid. Mobile phase B: 99.92% MeCN, 0.08% formic acid.

Gradient program (flow rate 25.0 mL/min), column temperature: ambient, variable gradient.

Method 8: Gemini C18 150×21.2 mm, 10 μm column. Mobile phase A: 99.9% ammonium formate, 0.1% formic acid. Mobile phase B: 94.9% MeCN, 0.1% formic acid, 5% mobile phase A.

Gradient program (flow rate 20.0 mL/min), column temperature: ambient, variable gradient.

Method 9: Luna C18(2) 250×21.2 mm, 5 μm column. Mobile phase A: 10 mM NH$_4$OAc, pH 5.8. Mobile phase B: 95% MeCN, 5% 200 mM NH$_4$OAc, pH 5.8.

Gradient program (flow rate 25.0 mL/min), column temperature: ambient, variable gradient.

INTERMEDIATE 1

Method A (2S)-2-Amino-3-(1H-indol-3-yl)propan-1-ol

To a stirred solution of (S)-tryptophan (4.0 g, 20.0 mmol) in THF (100 mL) at 0° C. was slowly added BH$_3$.Me$_2$S complex (5.9 mL, 10M solution in THF, 59.0 mmol). The reaction mixture was heated to 70° C. for 16 h and, after cooling, the excess borane was quenched by the addition of MeOH (10 mL) at 0° C. The reaction mixture was then concentrated in vacuo and the resultant white solid was dissolved in EtOAc (100 mL) and washed with aqueous NaOH solution (20% w/v, 2×70 mL). The organic fraction was then extracted into aqueous 2M HCl (2×100 mL). The combined acidic aqueous fractions were basified to pH 14 (addition of solid NaOH) and were re-extracted with EtOAc (2×150 mL). The combined organic fractions were washed with brine (70 mL), dried (MgSO$_4$), filtered and concentrated in vacuo to give the title compound (3.5 g, 92%) as a white solid that was used without further purification. δ$_H$ (CD$_3$OD) 7.46 (1H, d, J 7.9 Hz), 7.21 (1H, d, J 8.0 Hz), 6.96 (3H, m), 3.79 (1H, dd, J 11.3 Hz and J 3.6 Hz), 3.54 (1H, dd, J 11.2 Hz and J 6.2 Hz), 3.05 (1H, m), 2.80 (1H, m), 2.61 (1H, m). Exchangeable protons were not observed.

INTERMEDIATE 2

Method B

2-Chloro-N-[(1S)-2-hydroxy-1-(1H-indol-3-ylmethyl)ethyl]acetamide

To a stirred solution of Intermediate 1 (2.0 g, 10.0 mmol) and NEt$_3$ (1.3 g, 1.8 mL, 13.0 mmol) in THF (120 mL) at 0° C. was added chloroacetyl chloride (1.3 g, 1.0 mL, 12.0 mmol) dropwise. The reaction mixture was stirred at r.t. for 1.5 h and was then quenched by the addition of water (5 mL). The reaction mixture was diluted with EtOAc (120 mL) and partitioned with water (100 mL). The organic fraction was washed with brine (100 mL), dried (MgSO$_4$), filtered and concentrated in vacuo to give the title compound (2.4 g, 90%) as a beige solid that was used without further purification. δ$_H$ (CDCl$_3$) 8.15 (1H, br. s), 7.59 (1H, d, J 7.9 Hz), 7.28 (1H, d, J 8.0 Hz), 7.11 (3H, m), 6.97 (1H, d, J 2.3 Hz), 4.19 (1H, m), 3.92 (2H, d, J 2.9 Hz), 3.59 (2H, m), 2.98 (2H, d, J 6.0 Hz), 2.52 (1H, br. s).

INTERMEDIATE 3

Method C (5S)-5-(1H-Indol-3-ylmethyl)morpholin-3-one

To a stirred solution of Intermediate 2 (2.4 g, 9.5 mmol) in THF (100 mL) at 0° C. was added NaH (0.8 g, 60% dispersion in oil, 19.0 mmol) portionwise. The reaction mixture was stirred at r.t. for 1.5 h and then quenched at 0° C. by the addition of ice. The resulting mixture was partitioned between EtOAc (100 mL) and water (100 mL) and the organic fraction was dried (MgSO$_4$), filtered and concentrated in vacuo to give the title compound (1.8 g, 82%) as a yellow solid that was used without further purification. δ$_H$ (CD$_3$OD) 7.46 (1H, d, J 7.8 Hz), 7.25 (1H, d, J 7.8 Hz), 6.95 (3H, m), 3.99 (2H, s), 3.65 (2H, m), 3.52 (1H, m), 2.91 (2H, d, J 6.3 Hz). Exchangeable protons were not observed. MS (ES+) 231.0 (M+H)$^+$.

INTERMEDIATE 4

3-[(3S)-Morpholin-3-ylmethyl]-1H-indole

To a stirred solution of Intermediate 3 (1.8 g, 7.8 mmol) in THF (100 mL) at 0° C. was slowly added LiAlH$_4$ (1.0 g, 27.0 mmol). After stirring for 16 h at r.t., the reaction mixture was quenched by the dropwise addition of aqueous sat. NaHCO$_3$ solution (20 mL). The resulting mixture was filtered through Celite® and the filtrate was concentrated in vacuo. The resulting solid was azeotroped from toluene. Purification by column chromatography (SiO$_2$, EtOAc) gave the title compound (1.5 g, 89%) as a cream solid. δ$_H$ (CDCl$_3$) 8.11 (1H, br. s), 7.55 (1H, d, J 7.8 Hz), 7.28 (1H, d, J 8.0 Hz), 7.11 (3H, m), 3.83 (1H, dd, J 10.9 Hz and J 2.8 Hz), 3.71 (1H, dt, J 11.3 Hz and J 2.2 Hz), 3.47 (1H, m), 3.24 (1H, t, J 9.8 Hz), 3.06 (1H, m), 2.78 (3H, m), 2.56 (1H, m), 1.92 (1H, br. s). MS (ES+) 217.0 (M+H)$^+$.

INTERMEDIATE 5

(3S)-3-(1H-Indol-3-ylmethyl)morpholine-4-carbothioamide

To a stirred solution of 1,1'-thiocarbonyldiimidazole (28.6 g, 160.0 mmol) in THF (950 mL) was added Intermediate 4 (31.5 g, 145.8 mmol) in THF (300 mL) dropwise over 1 h. The reaction mixture was stirred at r.t. for 15 minutes and then concentrated in vacuo. A sat. solution of NH$_3$ in MeOH (600 mL) was added and the reaction mixture was stirred at 60° C. in a sealed flask for 12 h. The resulting mixture was then concentrated in vacuo and the oily residue purified by column chromatography (SiO$_2$, EtOAc) to give the title compound (17.6 g, 44%) as an orange foam. δ$_H$ (DMSO-d$_6$) 10.85 (1H, br. s), 7.86 (1H, d, J 7.2 Hz), 7.49 (2H, br. s), 7.33 (1H, d, J 8.0 Hz), 7.18 (1H, d, J 2.2 Hz), 7.09-7.01 (1H, m), 7.00-6.94 (1H, m), 3.87 (1H, m), 3.60 (1H, d, J 11.6 Hz), 3.36-3.18 (6H, m), 2.81 (1H, dd, J 13.6 Hz and J 4.8 Hz). MS (ES+) 276.0 $(M+H)^+$.

INTERMEDIATE 6

Ethyl 2-amino-4-methyl-1,3-thiazole-5-carboxylate

To a stirred solution of ethyl 2-chloroacetoacetate (6.0 mL, 43.35 mmol) in MeCN (24 mL) and THF (6 mL) was added thiourea (3.0 g, 39.41 mmol) and $Na_2CO_3$ (0.417 g, 39.41 mmol). The reaction mixture was heated at 120° C. under microwave irradiation for 30 minutes, cooled to r.t., partitioned between EtOAc and water, and the organic fraction was dried ($MgSO_4$), filtered and concentrated in vacuo to give the title compound (2.76 g, 38%) as a cream solid. $\delta_H$ ($CDCl_3$) 5.47 (2H, br. s), 4.27 (2H, q, J 7.2 Hz), 2.53 (3H, s), 1.33 (3H, t, J 7.2 Hz). MS (ES+) 187.0 $(M+H)^+$.

INTERMEDIATE 7

Ethyl 2-bromo-4-methyl-1,3-thiazole-5-carboxylate

To a stirred solution of Intermediate 6 (0.53 g, 2.85 mmol) in MeCN (6 mL) at 0° C. was added $CuBr_2$ (0.70 g, 3.13 mmol) followed by dropwise addition of tert-butyl nitrite (0.44 mL, 3.70 mmol). After stirring at 0° C. for 4 h, the reaction mixture was concentrated in vacuo to give a black oil. Purification by column chromatography ($SiO_2$, 0-50% EtOAc/hexanes) gave the title compound (0.54 g, 76%) as a yellow solid. $\delta_H$ ($CDCl_3$) 4.33 (2H, q, J 7.0 Hz), 2.71 (3H, s), 1.36 (3H, t, J 7.2 Hz). MS (ES+) 252.0 $(M+H)^+$.

INTERMEDIATE 8

2-Chloro-N-cyclopropyl-4-methyl-1,3-thiazole-5-carboxamide

To a stirred solution of Intermediate 7 (0.54 g, 2.16 mmol) in MeOH (5 mL), THF (1 mL) and water (1 mL) at r.t. was added NaOH (0.095 g, 2.38 mmol). After stirring for 2 h at r.t. the reaction mixture was neutralised with 1N HCl to pH 6 and the solvent removed in vacuo to give an off-white solid (0.2 g, 0.9 mmol). The solid was suspended in DCM (5 mL) and DMF (3 drops) was added, followed by oxalyl chloride (0.07 mL, 1.08 mmol). The reaction mixture was stirred at r.t. for 4 h, then cyclopropylamine (0.07 mL, 1.08 mmol) was added and stirred at r.t. for 1 h. The reaction mixture was concentrated in vacuo to give a yellow oil. Purification by column chromatography ($SiO_2$, 0-60% EtOAc/hexanes) gave the title compound (0.096 g, 21%) as a clear oil. $\delta_H$ (DMSO-$d_6$) 8.39 (1H, br. s), 2.76 (1H, m), 2.48 (3H, s), 0.69 (2H, m), 0.55 (2H, m). MS (ES+) 217.0 and 219.0 $(M+H)^+$.

INTERMEDIATE 9

2-Bromo-3-oxobutanamide

To a stirred solution of acetoacetamide (10.00 g, 98.9 mmol) in THF (200 mL) was added $NaHSO_4$ (2.97 g, 24.7 mmol). The reaction mixture was cooled to 0° C. and NBS (17.6 g, 98.9 mmol) was added portionwise. The reaction mixture was stirred at r.t. for 5.5 h then DCM (70 mL) and water (70 mL) were added. The aqueous layer was extracted with DCM (2×70 mL). The combined organic fractions were washed with water (3×100 mL), dried ($Na_2SO_4$), filtered and the solvent evaporated in vacuo. The residue was purified by column chromatography ($SiO_2$, 2:1 DCM/EtOAc) to give the title compound (11.78 g, 66%) as a cream solid. $\delta_H$ (DMSO-$d_6$) 7.91 (1H, br. s), 7.62 (1H, br. s), 5.15 (1H, s), 2.28 (3H, s). LCMS (ES+) 182.0 $(M+H)^+$, RT 2.07 minutes (Method 2).

INTERMEDIATE 10

N-Benzyl-D-serine

To a stirred solution of D-serine (14.7 g, 140.0 mmol) in aqueous 2M NaOH (70 mL) was added benzaldehyde (14.6 g, 14.0 mL, 138.0 mmol). The reaction mixture was then stirred at r.t. for 1 h before cooling to 5° C. $NaBH_4$ (1.5 g, 40.0 mmol) was added portionwise such that an internal temperature of between 6 and 10° C. was maintained. After addition, the reaction mixture was allowed to stir at 5° C. for 30 minutes and then at r.t. for 1 h. The reaction mixture was cooled to 5° C. and a further portion of $NaBH_4$ (1.5 g, 40.0 mmol) was added portionwise such that an internal temperature of <10° C. was maintained. The ice bath was removed on completion of addition and the reaction mixture stirred at r.t. for 16 h. The reaction mixture was then extracted with $Et_2O$ (3×100 mL) and the aqueous phase acidified to pH 5 with conc. HCl. The resultant white precipitate was filtered and washed with water. The product was dried in vacuo to give the title compound (24.0 g, 88%) as a white solid. $\delta_H$ (DMSO-$d_6$) 7.45-7.30 (5H, m), 4.04-3.91 (2H, m), 3.70-3.61 (3H, m), 3.17 (1H, t, J 5.8 Hz).

INTERMEDIATE 11

(3R)-4-Benzyl-5-oxomorpholine-3-carboxylic acid

To a stirred solution of Intermediate 10 (35.0 g, 179.0 mmol) in aqueous NaOH solution (9.3 g, 200.0 mL, 232.5 mmol) at 0° C. was slowly added chloroacetyl chloride (24.2 g, 17.0 mL, 214.0 mmol). The reaction mixture was allowed to warm to r.t. and then stirred for 30 minutes. Aqueous 10M NaOH solution (45.0 mL, 450.0 mmol) was added and the reaction mixture heated to 45° C. for 4 h. The reaction mixture was then cooled to 10° C. and acidified to pH 1 with conc. HCl. On standing at 4° C. the product crystallised from the mixture and was collected by filtration, washed with cold water and then dried in vacuo to give the title compound (18.0 g, 43%) as a white solid. $\delta_H$ (DMSO-$d_6$) 13.51-12.53 (1H, br. s), 7.38-7.25 (5H, m), 5.27 (1H, d, J 15.3 Hz), 4.24-4.10 (3H, m), 3.94-3.88 (2H, m), 3.83 (1H, d, J 15.3 Hz). MS (ES+) 236.0 $(M+H)^+$.

INTERMEDIATE 12

[(3S)-(4-Benzylmorpholin-3-yl)]methanol

To a stirred solution of Intermediate 11 (17.7 g, 75.3 mmol) in THF (300 mL) was added $NEt_3$ (7.3 g, 10.0 mL, 72.0 mmol). The solution was then cooled to 0° C. and $BH_3.Me_2S$ complex (10M in THF, 45.0 mL, 450.0 mmol) was added slowly. The reaction mixture was heated at reflux for 12 h and, after cooling to r.t., the excess borane was destroyed by slow addition of MeOH at 0° C. The reaction mixture was concentrated in vacuo and the resultant white solid was dissolved in EtOAc (120 mL) and washed with aqueous NaOH solution (20% v/v, 2×100 mL). The organic fraction was then extracted into aqueous 2M HCl (2×150 mL). The combined acidic aqueous fractions were then basified to pH 14 (addition of solid NaOH) and were re-extracted with EtOAc (2×150 mL). The combined organic fractions were washed with brine (150 mL), dried (MgSO$_4$), filtered and concentrated in vacuo to give the title compound (13.5 g, 87%) as a clear oil that required no further purification. $\delta_H$ (CDCl$_3$) 7.29-7.16 (5H, m), 4.05 (1H, d, J 12.8 Hz), 3.88 (1H, dd, J 11.5 Hz and J 4.5 Hz), 3.78 (1H, m), 3.70-3.53 (2H, m), 3.51-3.40 (2H, m), 3.20 (1H, d, J 13.2 Hz), 2.68 (1H, dt, J 12.1 Hz and J 2.8 Hz), 2.48 (1H, m), 2.27 (1H, m), 2.20-2.15 (1H, br. s).

INTERMEDIATE 13

(3S)-Morpholin-3-ylmethanol

To a solution of Intermediate 12 (10.0 g, 48.3 mmol) in MeOH (300 mL) was added 10 wt % palladium on carbon (2.0 g) and the reaction mixture placed in a Parr® apparatus under 50 psi of H$_2$ for 18 h. The resulting mixture was then filtered through Celite® and concentrated in vacuo to give the title compound (5.2 g, 92%) as a colourless oil. $\delta_H$ (CDCl$_3$) 3.81-3.76 (2H, m), 3.58-3.43 (3H, m), 3.35-3.28 (1H, m), 2.99-2.91 (5H, br. m). MS (ES+) 118.0 (M+H)$^+$.

INTERMEDIATE 14

(3aR)-Tetrahydro-3H-[1,2,3]oxathiazolo[4,3-c][1,4]oxazine 1,1-dioxide

To a solution of Intermediate 13 (30 g, 257 mmol) in DCM (250 mL) was added pyridine (43.5 mL, 539 mmol) and the reaction mixture was cooled to −70° C. Sulphuryl chloride (21.7 mL, 270 mmol) in DCM (200 mL) was added dropwise over 1 h (so as to maintain the reaction temperature below −60° C.). The reaction mixture was stirred at −70° C. for 2 h and at −10 to −20° C. for 2 h before being quenched by the addition of water (15 mL) and warming to r.t. The reaction mixture was separated and the aqueous fraction extracted with further DCM (2×100 mL). The combined organic fractions were washed with water (15 mL), brine (15 mL), dried (Na$_2$SO$_4$), filtered and concentrated in vacuo to give the title compound (24.7 g, 54%) as a yellow oil which solidified to an orange sticky solid on standing at r.t. that was used without further purification. $\delta_H$ (CDCl$_3$) 4.51 (1H, dd, J 8.1 Hz and J 6.4 Hz), 4.23 (1H, dd, J 9.1 Hz and J 8.1 Hz), 3.95 (1H, dd, J 11.6 Hz and J 3.4 Hz), 3.84-3.64 (3H, m), 3.54 (1H, dd, J 11.6 Hz and J 7.7 Hz), 3.29 (1H, dt, J 12.0 Hz and J 3.4 Hz), 3.06 (1H, m).

INTERMEDIATE 15

(3R)-3-[(3-Bromophenoxy)methyl]morpholine

To a stirred solution of 3-bromophenol (0.913 g, 5.28 mmol) in DMF (3 mL) at 0° C. was added NaH (0.221 g, 60% dispersion in oil, 5.53 mmol). The reaction mixture was stirred at 0° C. for 45 minutes then Intermediate 14 (0.860 g, 4.80 mmol) in DMF (5 mL) was added. The reaction mixture was stirred at r.t. for 1 h, then at 60° C. for 3 h and then concentrated in vacuo. MeOH (8 mL) followed by aqueous HCl (2N, 8 mL) were added to the residue. The reaction mixture was stirred at r.t. for 3 days and concentrated again in vacuo. DCM (15 mL) and sat. aqueous NaHCO$_3$ (15 mL) were added and the aqueous layer was extracted with DCM (2×10 mL). The combined organic fractions were washed with water (3×15 mL), dried (Na$_2$SO$_4$) and the solvent evaporated in vacuo to give a light yellow oil (1.3 g, quantitative) that was used as a crude intermediate. LCMS (ES+) 272.0 (M+H)$^+$, RT 1.93 minutes (Method 2).

INTERMEDIATE 16

3-Bromo-L-phenylalanine (2S)-3-(3-Bromophenyl)-2-(tert-butoxycarbonylamino) propionic acid (5.0 g, 14.5 mmol) was suspended in 4M HCl in 1,4-dioxane (75 mL) and stirred for 16 h at r.t. The white precipitate was filtered and washed with Et$_2$O to give the title compound (3.2 g, 89%) as a white solid that required no further purification. $\delta_H$ (CDCl$_3$) 8.32 (2H, s), 7.50-7.48 (2H, m), 7.34-7.29 (2H, m), 4.22 (1H, t, J 6.2 Hz), 3.13-3.11 (2H, m).

INTERMEDIATE 17

(2S)-2-Amino-3-(3-bromophenyl)propan-1-ol

The title compound was prepared from Intermediate 16 according to Method A and was isolated as a colourless oil (56%) that required no further purification. $\delta_H$ (CDCl$_3$) 7.42-7.35 (2H, m), 7.29-7.19 (2H, m), 3.59 (1H, m), 3.39 (1H, m), 3.10 (1H, m), 2.78 (1H, dd, J 13.5 Hz and J 5.3 Hz), 2.51 (1H, dd, J 13.5 Hz and J 8.5 Hz).

INTERMEDIATE 18

N-[(1S)-1-(3-Bromobenzyl)-2-hydroxyethyl]-2-chloroacetamide

The title compound was prepared from Intermediate 17 according to Method B and was isolated as a yellow oil (77%) after purification by column chromatography (SiO$_2$, 1:1 EtOAc/DCM). $\delta_H$ (DMSO-d$_6$) 8.06 (1H, d, J 8.4 Hz), 7.42 (1H, s), 7.39-7.35 (1H, m), 7.26-7.19 (2H, m), 4.85 (1H, t, J 5.6 Hz), 3.98 (2H, s), 3.87 (1H, m), 3.39-3.15 (2H, m), 2.84 (1H, dd, J 13.7 Hz and J 5.4 Hz), 2.65 (1H, dd, J 13.7 Hz and J 8.6 Hz).

INTERMEDIATE 19

(5S)-5-(3-Bromobenzyl)morpholin-3-one

The title compound was prepared from Intermediate 18 according to Method C and was isolated as a white solid (50%) after purification by column chromatography (SiO$_2$, 1:1 EtOAc/DCM). $\delta_H$ (CDCl$_3$) 7.36-7.32 (1H, m), 7.28 (1H, s), 7.19-7.11 (1H, m), 7.06-7.03 (1H, m), 6.26 (1H, br. s), 4.09 (2H, s), 3.81 (1H, dd, J 11.7 Hz and J 3.6 Hz), 3.71-3.62 (1H, m), 3.50 (1H, dd, J 11.6 Hz and J 6.0 Hz), 2.79 (1H, dd, J 13.6 Hz and J 6.1 Hz), 2.67 (1H, dd, J 13.6 Hz and J 8.2 Hz). MS (ES+) 270.0 and 272.0 (M+H)$^+$.

INTERMEDIATE 20

(3S)-3-(3-Bromobenzyl)morpholine

To a stirred solution of Intermediate 19 (0.8 g, 3.0 mmol) in THF (100 mL) at 0° C. was added BH$_3$.Me$_2$S complex (1.7 mL, 10 M solution in THF, 17.7 mmol) dropwise. The reaction was then carried out according to Method A to give the title compound (0.7 g, 83%) as a colourless oil. MS (ES+) 256.0 and 258.0 (M+H)$^+$.

INTERMEDIATE 21

(3S)-3-(3-Bromobenzyl)morpholine-4-carbothioamide

To a stirred solution of 1,1'-thiocarbonyldiimidazole (13.31 g, 74.8 mmol) in THF (250 mL) was added dropwise over a period of 30 minutes a solution of Intermediate 20 (17.35 g, 68.0 mmol) in THF (250 mL). The reaction mixture was stirred at r.t. for 24 h then evaporated in vacuo. The residue was redissolved in MeCN (200 mL) and aqueous $NH_3$ (17% v/v, 300 mL) was added. The reaction mixture was heated at 60° C. for 8 h. Another portion of aqueous $NH_3$ (20 mL) was added and the mixture was stirred at r.t. for 24 h then evaporated in vacuo. The residue was redissolved in DCM (200 mL) and the resulting mixture was washed with sat. aqueous $NH_4Cl$ solution (2×150 mL), dried ($Na_2SO_4$), filtered and the solvent evaporated in vacuo to give the title compound (22 g, quantitative) as a yellow solid which was used as a crude intermediate. LCMS (ES+) $(M+H)^+$, 315.0 and 317.0 (1:1 ratio), RT 2.69 minutes (Method 2).

INTERMEDIATE 22

(3R)-3[(3-Bromophenoxy)methyl]morpholine-4-carbothioamide

To a stirred solution of Intermediate 15 (1.30 g, 4.76 mmol) in THF (20 mL) was added 1,1'-thiocarbonyldiimidazole (0.932 g, 5.24 mmol). The reaction mixture was stirred at r.t. for 24 h then evaporated in vacuo. The residue was redissolved in MeCN (10 mL) and aqueous $NH_3$ (17% v/v, 15 mL) was added. The resulting mixture was heated at 60° C. for 16 h, cooled, filtered, washed with water (2×5 mL), dried at 50° C. to give the title compound (1.0 g, 64%) as a white solid that required no further purification. LCMS (ES+) 333.0 $(M+H)^+$, RT 2.77 minutes (Method 2).

INTERMEDIATE 23

(3S)-3-(Prop-2-yn-1-yl)morpholine

To a solution of (trimethylsilyl)acetylene (27.59 mL, 195.25 mmol) in THF (250 mL) at 0° C. was added n-butyllithium (78.1 mL, 201 mmol, 2.5M in hexanes) dropwise over 15 minutes. After stirring at this temperature for 40 minutes, a solution of Intermediate 14 (11.65 g, 65.08 mmol) in DMPU (11 mL) was added slowly over 15 minutes and the reaction mixture was allowed to warm to r.t. After stirring at r.t. for 18 h, the reaction mixture was quenched by the addition of water (about 4 mL) and the solvent (not DMPU) was removed in vacuo. To the resultant dark oil were added aqueous HCl (10% v/v, 200 mL) and MeOH (100 mL) and the reaction mixture was stirred at r.t. for 18 h and then concentrated in vacuo to give the title compound (17.059 g, ~74% yield) as a crude dark oil (containing about 11 mL DMPU) that was used without further purification. $\delta_H$ ($CD_3OD$) 3.89 (1H, dd, J 11.2 Hz and J 3.1 Hz), 3.76 (1H, dt, J 11.2 Hz and J 2.7 Hz), 3.45-3.56 (1H, m), 3.25 (1H, m), 2.89 (3H, m), 2.39 (1H, t, J 2.7 Hz), 2.25 (2H, dd, J 6.8 Hz and J 2.7 Hz). Exchangeable proton was not observed.

INTERMEDIATE 24 tert-Butyl (3S)-3-(prop-2-yn-1-yl)morpholine-4-carboxylate

To a solution of crude Intermediate 23 (17.059 g, containing 11 mL DMPU) in DCM (300 mL) at 0° C. was added DIPEA (13.04 mL, 74.85 mmol) and di-tert-butyl dicarbonate (15.624 g, 71.59 mmol) and the reaction mixture warmed to r.t. After stirring for 18 h, the reaction mixture was washed with brine and the organic fraction was passed through an Isolute® phase separator cartridge and concentrated in vacuo to give a dark brown oil. Purification by column chromatography ($SiO_2$, 1:10 EtOAc/hexanes) gave the title compound (8.79 g, 59% from Intermediate 14) as a yellow oil. $\delta_H$ ($CD_3OD$) 3.95 (1H, m), 3.75 (1H, d, J 14.2 Hz), 3.70 (1H, m), 3.58 (1H, m), 3.42 (1H, m), 3.30 (1H, m), 2.95 (1H, m), 2.51 (1H, m), 2.37 (1H, m), 2.19 (1H, t, J 2.7 Hz), 1.35 (9H, s).

INTERMEDIATE 25

Method D tert-Butyl (3S)-3-[3-(trimethylsilyl)prop-2-yn-1-yl]morpholine-4-carboxylate To a solution of Intermediate 24 (8.05 g, 35.7 mmol) in THF (250 mL) at 0° C. was added n-butyllithium (15.7 mL, 39.3 mmol, 2.5M in hexanes) dropwise over 15 minutes. After stirring for 30 minutes, chlorotrimethylsilane was added slowly over 5 minutes and the reaction mixture stirred for 45 minutes and then allowed to warm to r.t. After stirring at r.t. for 18 h, the reaction mixture was quenched by the addition of water (about 1 mL) and the solvent was removed in vacuo. The crude mixture was dissolved in DCM and washed with water, the aqueous phase was extracted with further DCM (500 mL) and the combined organic fractions were passed through an Isolute® phase separator cartridge and concentrated in vacuo to give a dark brown oil. Purification by column chromatography ($SiO_2$, 5-20% EtOAc/hexanes) gave the title compound (8.1 g, 76%) as a colourless oil and recovered starting material (1.25 g, 15%). $\delta_H$ ($CD_3OD$) 3.91 (1H, m), 3.82 (1H, d, J 11.7 Hz), 3.70 (1H, dd, J 11.4 Hz and J 3.6 Hz), 3.58 (1H, dd, J 13.7 Hz and J 2.9 Hz), 3.40-3.20 (2H, m), 2.95 (1H, m), 2.60 (1H, dd, J 16.7 Hz and J 9.1 Hz), 2.38 (1H, dd, J 16.7 Hz and J 6.4 Hz), 1.35 (9H, s), 0.00 (9H, s).

INTERMEDIATE 26

Method E

Methyl 3-{[(3S)-4-(tert-butoxycarbonyl)morpholin-3-yl]methyl}-2-(trimethylsilyl)-1H-indole-5-carboxylate To a solution of Intermediate 25 (4.4 g, 14.8 mmol) dissolved in DMF (25 mL) was added methyl 4-amino-3-iodobenzoate (4.1 g, 14.8 mmol), LiCl (0.627 g, 14.8 mmol), $Na_2CO_3$ (3.1 g, 29.6 mmol) and $Pd(OAc)_2$ (0.130 g, 0.59 mmol) and the reaction mixture was degassed under vacuum and then purged with nitrogen. The reaction mixture was then heated at 100° C. for 16 h. The crude reaction mixture was cooled to r.t. and the solvent removed in vacuo to give a brown oil. The crude residue was partitioned between DCM (200 mL) and water (100 mL) and the organic fraction was dried using an Isolute® phase separator cartridge and concentrated in vacuo to give a dark brown oil. Purification by column chromatography ($SiO_2$, 10-25% EtOAc/hexanes) gave the title compound (3.90 g, 59%) as a yellow sticky solid. LCMS (ES+) 392.0 $((M-^tBu)+H)^+$, RT 3.58 minutes (Method 2).

INTERMEDIATE 27

Method F

Methyl 3-[(3S)-morpholin-3-ylmethyl]-1H-indole-5-carboxylate

To Intermediate 26 (3.90 g, 8.73 mmol) in MeOH (15 mL) was added 4M HCl in 1,4-dioxane (20 mL) and the reaction mixture was stirred at r.t. for 4 h. The reaction mixture was concentrated in vacuo and the crude residue was dissolved in DCM (100 mL) and washed with aqueous sat. NaHCO$_3$ solution (20 mL). The aqueous fraction was further extracted with DCM (3×50 mL) and the combined organic fractions were dried (Na$_2$SO$_4$), filtered and concentrated in vacuo to give the title compound (2.40 g, quantitative) as a pale brown gum that was used without further purification. LCMS (ES+) 275.0 (M+H)$^+$, RT 2.30 minutes (Method 4).

INTERMEDIATE 28

Method G

Methyl 3-{[(3S)-4-(aminocarbonothioyl)morpholin-3-yl]methyl}-1H-indole-5-carboxylate To a solution of 1,1'-thiocarbonyldiimidazole (1.71 g, 9.60 mmol) in THF (20 mL) was added Intermediate 27 (2.39 g, 8.73 mmol) dissolved in THF (10 mL) and the reaction mixture was stirred at r.t. for 16 h. The reaction mixture was concentrated in vacuo and dissolved in MeCN (50 mL) and aqueous NH$_3$ (20% v/v, 30 mL) added. The reaction mixture was stirred at 60° C. for 6 h. After cooling to r.t., the reaction mixture was concentrated in vacuo. The crude material was purified by column chromatography (SiO$_2$, 0-8% MeOH/DCM) to give the title compound (2.90 g, 99%) as a yellow solid. LCMS (ES+) 334.0 (M+H)$^+$, RT 2.25 minutes (Method 3).

INTERMEDIATE 29

Methyl 3-{[(3S)-4-(tert-butoxycarbonyl)morpholin-3-yl]methyl}-2-(trimethylsilyl)-1H-indole-6-carboxylate The title compound was prepared from methyl 3-amino-4-iodobenzoate and Intermediate 25 according to Method E and was isolated as a yellow solid (77%) after purification by column chromatography (SiO$_2$, 10% EtOAc/hexanes). $\delta_H$ (DMSO-d$_6$) 10.98 (1H, s), 8.07 (1H, s), 7.75 (1H, br. s), 7.57 (1H, d, J 8.3 Hz), 4.10 (1H, m), 3.88 (1H, d, J 10.9 Hz), 3.86 (3H, s), 3.74 (1H, m), 3.50 (1H, m), 3.33 (4H, m), 2.85 (1H, br. s), 1.32 (9H, br. s), 0.41 (9H, s). LCMS (ES+) 469.0 (M+Na)$^+$, RT 3.97 minutes (Method 4).

INTERMEDIATE 30

Methyl 3-[(3S)-morpholin-3-ylmethyl]-1H-indole-6-carboxylate

The title compound was prepared from Intermediate 29 according to Method F and was isolated as an orange oil (84%) that was used as a crude intermediate. $\delta_H$ (DMSO-d$_6$) 11.27 (1H, s), 8.00 (1H, s), 7.60 (2H, m), 7.39 (1H, d, J 2.1 Hz), 3.83 (3H, s), 3.61 (2H, d, J 10.8 Hz), 3.33 (1H, m), 3.07 (1H, t, J 10.2 Hz), 2.89 (1H, m), 2.67 (4H, br. m). LCMS (ES+) 275.0 (M+H)$^+$, RT 2.17 minutes (Method 4).

INTERMEDIATE 31

Methyl 3-{[(3S)-4-(aminocarbonothioyl)morpholin-3-yl]methyl}-1H-indole-6-carboxylate The title compound was prepared from Intermediate 30 according to Method G and was isolated as a yellow foam (76%) after purification by column chromatography (SiO$_2$, 5% MeOH/DCM). $\delta_H$ (DMSO-d$_6$) 11.18 (1H, s), 8.04 (1H, d, J 0.8 Hz), 7.88 (1H, d, J 8.4 Hz), 7.61 (1H, dd, J 8.4 Hz and J 1.4 Hz), 7.44 (1H, d, J 2.2 Hz), 7.30 (2H, s), 4.99 (1H, m), 4.20 (1H, m), 3.91 (1H, d, J 8.1 Hz), 3.87 (3H, s), 3.63 (1H, d, J 11.7 Hz), 3.38 (3H, m), 3.26 (1H, m), 2.92 (1H, dd, J 13.7 Hz and J 4.7 Hz). LCMS (ES+) 334.0 (M+H)$^+$, RT 2.75 minutes (Method 4).

INTERMEDIATE 32

Benzyl (3S)-3-(prop-2-yn-1-yl)morpholine-4-carboxylate

To a solution of crude Intermediate 23 (2.806 g) dissolved in DCM (50 mL) cooled to 0° C. was added NEt$_3$ (6.5 mL, 46.8 mmol) followed by benzyl chloroformate (4.85 mL, 33.9 mmol). The mixture was stirred at r.t. for 18 h. The reaction mixture was diluted further with DCM (100 mL) and washed with aqueous sat. NaHCO$_3$ solution (20 mL). The aqueous fraction was further extracted with DCM (3×50 mL). The combined organic fractions were concentrated in vacuo to give a brown oil. The crude material was purified by column chromatography (SiO$_2$, 0.5-1% MeOH/DCM; followed by SiO$_2$, EtOAc) to yield the title compound (4.01 g, 68% from Intermediate 14) as a yellow oil. $\delta_H$ (DMSO-d$_6$) 7.42-7.27 (5H, m), 4.73 (2H, br. s), 4.03-3.97 (1H, m), 3.77-3.74 (2H, m), 3.64 (1H, dd, J 13.6 Hz and J 2.6 Hz), 3.44 (1H, dd, J 11.7 Hz and J 3.1 Hz), 3.35-3.26 (1H, m), 3.09-3.03 (1H, m), 2.83 (1H, t, J 2.6 Hz), 2.58-2.57 (1H, m), 2.48-2.46 (1H, m). LCMS (ES+) 260.1 (M+H)$^+$, RT 3.25 minutes (Method 4).

INTERMEDIATE 33

Benzyl (3S)-3-[3-(trimethylsilyl)prop-2-yn-1-yl]morpholine-4-carboxylate

The title compound was prepared from Intermediate 32 according to Method D and was isolated as a yellow oil (12%) after purification by column chromatography (SiO$_2$, 1:10 EtOAc/hexanes). $\delta_H$ (CD$_3$OD) 7.28-7.15 (5H, m), 5.03 (2H, br. s), 4.06-4.00 (1H, m), 3.79-3.70 (1H, m), 3.66 (1H, dd, J 13.7 Hz and J 3.0 Hz), 3.42 (1H, dd, J 12.0 Hz and J 3.2 Hz), 3.32 (1H, dt, J 12.0 Hz and J 3.0 Hz), 3.20 (1H, quint, J 1.6 Hz), 3.10-3.00 (1H, m), 2.63-2.54 (2H, m), 0.00 (9H, s). LCMS (ES+) 332.0 (M+H)$^+$, RT 3.83 minutes (Method 4).

INTERMEDIATE 34

Benzyl (3S)-3-{[5-(trifluoromethoxy)-2-(trimethylsilyl)-1H-indol-3-yl]methyl}-morpholine-4-carboxylate The title compound was prepared from Intermediate 33 and 2-iodo-4-trifluoromethoxyaniline according to Method E and was isolated as a yellow oil (46%) after purification by column chromatography (SiO$_2$, 5-10% EtOAc/hexanes). $\delta_H$ (CD₃OD) 7.70-7.40 (1H, br. m), 7.29-7.19 (6H, m), 6.89-6.86 (1H, m), 5.07 (2H, s), 4.13-4.00 (1H, m), 3.83-3.77 (2H, m), 3.55-3.51 (1H, m), 3.44-3.26 (4H, m), 2.89-2.75 (1H, m), 0.28 (9H, s). Exchangeable proton was not observed. LCMS (ES+) 507.0 (M+H)⁺, RT 4.12 minutes (Method 4).

INTERMEDIATE 35

3-[(3S)-Morpholin-3-ylmethyl]-5-(trifluoromethoxy)-1H-indole

To a solution of Intermediate 34 (0.290 g, 0.57 mmol) dissolved in MeCN (8 mL) at 0° C. was added iodotrimethylsilane (0.312 mL, 2.29 mmol) and the reaction mixture was stirred at 0° C. for 4 h. Aqueous HCl (10% v/v, 2 mL) was added to the reaction mixture at 0° C. and the aqueous fraction extracted with Et₂O (20 mL). The aqueous fraction was basified with aqueous 2M NaOH (5 mL) and extracted with DCM (30 mL). The organic fraction was concentrated in vacuo to yield the title compound (0.160 g, 93%) as a yellow oil. The crude material was used without further purification. $\delta_H$ (CD₃OD) 7.47 (1H, s), 7.40 (1H, d, J 8.8 Hz), 7.22 (1H, s), 7.02 (1H, dd, J 8.8 Hz and J 1.1 Hz), 3.82-3.74 (2H, m), 3.59-3.46 (1H, m), 3.39-3.24 (1H, m), 3.10-3.01 (1H, m), 2.88-2.84 (2H, m), 2.81-2.73 (2H, m). Exchangeable protons were not observed. LCMS (ES+) 301.0 (M+H)⁺, RT 2.38 minutes (Method 4).

INTERMEDIATE 36

(3S)-3-{[5-(Trifluoromethoxy)-1H-indol-3-yl]methyl}morpholine-4-carbothioamide

The title compound was prepared from Intermediate 35 according to Method G (at 50° C.) and was isolated as a colourless oil (53%) after purification by column chromatography (SiO₂, 30-50% EtOAc/DCM). $\delta_H$ (CDCl₃) 8.39 (1H, br. s), 7.63 (1H, br. s), 7.27 (1H, d, J 8.8 Hz), 7.12 (1H, d, J 2.3 Hz), 6.99 (1H, dd, J 8.8 Hz and J 1.1 Hz), 5.63 (2H, br. s), 3.98-3.86 (1H, m), 3.77 (1H, d, J 11.9 Hz), 3.52-3.38 (3H, m), 3.20-3.04 (2H, m). LCMS (ES+) 360.0 (M+H)⁺, RT 2.52 minutes (Method 2).

INTERMEDIATE 37

6-Bromo-4H-benzo[1,4]oxazin-3-one

NEt₃ (2.4 mL, 17 mmol) was added to 2-amino-4-bromophenol (2.5 g, 13 mmol) in THF (80 mL). The reaction mixture was cooled to 0° C., chloroacetyl chloride (1.12 mL, 14 mmol) was added portionwise and then stirred at 0° C. for 10 minutes before being allowed to warm to r.t. and stirred for a further 2 h. The reaction mixture was cooled to 0° C. and NaH (1.05 g, 60% dispersion in oil, 26 mmol) was added portionwise. The reaction mixture was stirred at 0° C. for 20 minutes then at r.t. for 2 h before being quenched with water (20 mL). The solvent was removed in vacuo and the resulting mixture diluted with water (100 mL). The precipitate was filtered, washed with water (3×50 mL) and dried in vacuo to give the title compound (2.14 g, 70%) as a beige solid. $\delta_H$ (DMSO-d₆) 10.81 (1H, br. s), 7.08 (1H, dd, J 8.5 Hz and J 2.3 Hz), 7.02 (1H, d, J 2.3 Hz), 6.92 (1H, d, J 8.5 Hz), 4.60 (2H, s).

INTERMEDIATE 38

6-Bromo-3,4-dihydro-2H-benzo[1,4]oxazine

Borane-THF (13.2 mL, 1M solution in THF, 13.2 mmol) was added portionwise to Intermediate 37 (2.0 g, 8.0 mmol) in THF (50 mL) at r.t. The resulting mixture was stirred at r.t. for 10 minutes, heated to reflux for 1 h and then allowed to cool to r.t. The reaction mixture was cooled to 0° C. and quenched with water (20 mL) and aqueous 2N NaOH (20 mL). The solvent was removed in vacuo and the resulting mixture diluted with water (100 mL). The aqueous fraction was extracted with EtOAc (100 mL), washed with brine (100 mL), dried (MgSO₄), filtered and concentrated in vacuo to yield the title compound (2 g, quantitative) as a brown oil. $\delta_H$ (DMSO-d₆) 6.68 (3H, m), 4.25-4.18 (2H, m), 3.81 (1H, br. s), 3.44-3.36 (2H, m).

INTERMEDIATE 39

6-Bromo-2,3-dihydrobenzo[1,4]oxazine-4-carbothioic acid amide

Intermediate 38 (1.7 g, 8 mmol) and 1,1'-thiocarbonyldiimidazole (2.84 g, 16 mmol) were dissolved in THF (15 mL) and heated to 120° C. under microwave irradiation for 15 minutes. After cooling to r.t., NH₃ (40 mL, 7N solution in MeOH, 280 mmol) was added, and the mixture stirred at r.t. for 3 h. The reaction mixture was concentrated in vacuo and then partitioned between EtOAc (100 mL) and water (100 mL). The organic fraction was washed with water (100 mL) and brine (100 mL), dried (MgSO₄), filtered and concentrated in vacuo. The residue was triturated with Et₂O and heptane to give the title compound (0.5 g, 23%) as a white solid. $\delta_H$ (DMSO-d₆) 8.20 (2H, br. s), 7.60 (1H, d, J 2.3 Hz), 7.21 (1H, dd, J 8.7 Hz and J 2.3 Hz), 6.88 (1H, d, J 8.9 Hz), 4.30-4.16 (4H, m).

INTERMEDIATE 40 tert-Butyl (3S)-3-{[5-cyano-2-(trimethylsilyl)-1H-indol-3-yl]methyl}morpholine-4-carboxylate The title compound was prepared from Intermediate 25 and 4-amino-3-iodobenzonitrile according to Method E and was isolated as a yellow solid (50%) after purification by column chromatography (SiO₂, 5-100% EtOAc/hexanes). LCMS (ES+) 414.0 (M+H)⁺, RT 3.92 minutes (Method 4).

INTERMEDIATE 41

3-[(3S)-Morpholin-3-ylmethyl]-1H-indole-5-carbonitrile

The title compound was prepared from Intermediate 40 according to Method F and was isolated as a brown solid (87%) that was used without further purification. LCMS (ES+) 242.0 (M+H)⁺, RT 2.15 minutes (Method 4).

INTERMEDIATE 42

(3S)-3-[(5-Cyano-1H-indol-3-yl)methyl]morpholine-4-carbothioamide

The title compound was prepared from Intermediate 41 according to Method G and was isolated as an off-white solid (39%) after purification by column chromatography (SiO₂, 0-5% MeOH/DCM). LCMS (ES+) 301.0 (M+H)⁺, RT 2.77 minutes (Method 4).

INTERMEDIATE 43 tert-Butyl (3S)-3-{[6-methoxy-2-(trimethylsilyl)-1H-indol-3-yl]methyl}morpholine-4-carboxylate The title compound was prepared from Intermediate 25 and 2-iodo-5-methoxyaniline according to Method E and was isolated as a clear glass (80%) after purification by column chromatography (SiO$_2$, 0-10% EtOAc/hexanes). LCMS (ES+) 419.1 (M+H)$^+$, RT 3.87 minutes (Method 4).

INTERMEDIATE 44

6-Methoxy-3-[(3S)-morpholin-3-ylmethyl]-1H-indole

The title compound was prepared from Intermediate 43 according to Method F and was isolated as a white foam (97%) that was used without further purification. LCMS (ES+) 247.1 (M+H)$^+$, RT 2.07 minutes (Method 5).

INTERMEDIATE 45

3-[(6-Methoxy-1H-indol-3-yl)methyl]morpholine-4-carbothioamide

The title compound was prepared from Intermediate 44 according to Method G and was isolated as a pale yellow solid (47%) that was used without further purification. LCMS (ES+) 306.0 (M+H)$^+$, RT 2.74 minutes (Method 4).

INTERMEDIATE 46

1-(4-Amino-3-iodophenyl)ethanone

To a stirred suspension of CaCO$_3$ (4.5 g, 45.27 mmol) in H$_2$O (15 mL) was added a solution of 4-acetylaniline (4.1 g, 30.18 mmol) in MeOH (25 mL), followed by a solution of iodine monochloride (5.2 g, 31.88 mmol) in MeOH (20 mL) dropwise. The reaction was stirred at r.t. for 45 minutes, then diluted with Et$_2$O (150 mL). The organic fraction was separated, washed with water (100 mL), then brine (100 mL), dried (Na$_2$SO$_4$), filtered and concentrated in vacuo to give the title compound (3.5 g, 44%) as a brown oil that was used without further purification. $\delta_H$ (DMSO-d$_6$) 8.14 (1H, d, J 1.8 Hz), 7.70 (1H, dd, J 8.3 and 1.8 Hz), 6.75 (1H, d, J 8.3 Hz), 6.10 (2H, s), 2.41 (3H, s). LCMS (ES+) 261 (M)$^+$, 283 (M+Na)$^+$, RT 3.026 minutes (Method 4).

INTERMEDIATE 47 tert-Butyl (3S)-3-{[5-acetyl-2-(trimethylsilyl)-1H-indol-3-yl]methyl}morpholine-4-carboxylate The title compound was prepared from Intermediate 25 and Intermediate 46 according to Method E and was isolated as a yellow oil (61%) after purification by column chromatography (SiO$_2$, 10% EtOAc/hexanes). LCMS (ES+) 453.0 (M+Na)$^+$, 375 ((M−$^t$Bu)+H)$^+$, RT 3.87 minutes (Method 5).

INTERMEDIATE 48

1-{3-[(3S)-Morpholin-3-ylmethyl]-1H-indol-5-yl}ethanone

The title compound was prepared from Intermediate 47 according to Method F and was isolated as a brown oil (95%) that was used without further purification. $\delta_H$ (DMSO-d$_6$) 11.12 (1H, s), 8.13 (1H, s), 7.60 (1H, d, J 8.6 Hz), 7.28 (1H, d, J 8.6 Hz), 7.15 (1H, d, J 1.7 Hz), 3.54-3.49 (2H, m), 3.44 (2H, s), 3.00 (1H, t, J 10.0 Hz), 2.83-2.78 (1H, m), 2.64-2.51 (4H, m), 2.51 (3H, s). LCMS (ES+) 259.0 (M+H)$^+$, RT 2.12 minutes (Method 4).

INTERMEDIATE 49

(3S)-3-[(5-Acetyl-1H-indol-3-yl)methyl]morpholine-4-carbothioamide

The title compound was prepared from Intermediate 48 according to Method G and was isolated as a brown oil (81%) after purification by column chromatography (SiO$_2$, 0-10% MeOH/DCM). LCMS (ES+) 318.1 (M+H)$^+$, RT 2.68 minutes (Method 4).

INTERMEDIATE 50 tert-Butyl (3S)-3-{[2,2-difluoro-6-(trimethylsilyl)-5H-[1,3]dioxolo[4,5-f]indol-7-yl]methyl}morpholine-4-carboxylate The title compound was prepared from 2,2-difluoro-5-amino-6-iodo-1,3-benzodioxole and Intermediate 25 according to Method E and was isolated as a yellow gum (30%) after purification by column chromatography (SiO$_2$, 5-20% EtOAc/hexanes). LCMS (ES+) 414.0 ((M−$^t$Bu)+H)$^+$, RT 4.34 minutes (Method 4).

INTERMEDIATE 51

2,2-Difluoro-7-[(3S)-morpholin-3-ylmethyl]-5H-[1,3]dioxolo[4,5-f]indole

The title compound was prepared from Intermediate 50 according to Method F and was isolated as a brown gum (quantitative) that was used without further purification. LCMS (ES+) 297.0 (M+H)$^+$, RT 2.08 minutes (Method 2).

INTERMEDIATE 52

(3S)-3-[(2,2-Difluoro-5H-[1,3]dioxolo[4,5-f]indol-7-yl)methyl]morpholine-4-carbothioamide The title compound was prepared from Intermediate 51 according to Method G and was isolated as a yellow gum (58%) after purification by column chromatography (SiO$_2$, 0-2% MeOH/DCM). LCMS (ES+) 356.0 (M+H)$^+$, RT 3.03 minutes (Method 4).

INTERMEDIATE 53

1-(4-Amino-3-iodophenyl)-2,2,2-trifluoroethanone

To a stirred solution of 1-(4-aminophenyl)-2,2,2-trifluoroethanone (1.0 g, 5.28 mmol) in 1M aqueous HCl solution (70 mL) was added iodine monochloride (0.77 g, 4.76 mmol). The reaction mixture was stirred at r.t. for 2 h, then basified with the addition of aqueous sat. NaHCO$_3$ solution and extracted with EtOAc (2×100 mL). The combined organic fractions were dried (Na$_2$SO$_4$), filtered and concentrated in vacuo. Purification by column chromatography (SiO$_2$, 15-20% EtOAc/hexanes) gave the title compound (0.983 g, 59%) as a cream solid. $\delta_H$ (CDCl$_3$) 8.40 (1H, d, J 1.0 Hz), 7.92-7.85 (1H, m), 6.76 (1H, d, J 8.6 Hz), 4.91 (2H, br. s). LCMS (ES+) RT 2.86 minutes (Method 2).

INTERMEDIATE 54 tert-Butyl (3S)-3-{[5-(trifluoroacetyl)-2-(trimethylsilyl)-1H-indol-3-yl]methyl}morpholine-4-carboxylate The title compound was prepared from Intermediate 25 and Intermediate 53 according to Method E and was isolated as a yellow gum (88%) after purification by column chromatography (SiO$_2$, 10-15% EtOAc/hexanes). LCMS (ES+) 429.1 ((M−$^t$Bu)+H)$^+$, RT 3.50 minutes (Method 2).

INTERMEDIATE 55

2,2,2-Trifluoro-1-{3-[(3S)-morpholin-3-ylmethyl]-1H-indol-5-yl}ethanone

The title compound was prepared from Intermediate 54 according to Method F and was isolated as a yellow gum (76%) that was used without further purification. LCMS (ES+) 313.0 (M+H)$^+$, RT 1.89 minutes (Method 2).

INTERMEDIATE 56

(3S)-3-{[5-(Trifluoroacetyl)-1H-indol-3-yl]methyl}morpholine-4-carbothioamide

The title compound was prepared from Intermediate 55 according to Method G and was isolated as a yellow gum (84%) after purification by column chromatography (SiO$_2$, 0-5% MeOH/DCM). LCMS (ES+) 372.2 (M+H)$^+$, RT 2.44 minutes (Method 2).

INTERMEDIATE 57

N-(6-Iodo-1,3-benzodioxol-5-yl)acetamide

To a stirred solution of 3',4'-methylenedioxyacetanilide (7.7 g, 43.0 mmol) in DCM (100 mL) and AcOH (6.5 mL) was added a solution of iodine monochloride (6.3 g, 38.8 mmol) in DCM (50 mL). The reaction mixture was stirred at r.t. for 16 h. Aqueous sat. Na$_2$S$_2$O$_3$ (500 mL) was added. The organic fraction was separated, dried (Na$_2$SO$_4$), filtered and concentrated in vacuo. Purification by column chromatography (SiO$_2$, 50% EtOAc/hexanes) gave the title compound (7.5 g, 57%) as a brown solid. LCMS (ES+) 306.0 (M+H)$^+$, RT 2.75 minutes (Method 4).

INTERMEDIATE 58

6-Iodo-1,3-benzodioxol-5-amine

To a stirred solution of Intermediate 57 (5.0 g, 16.4 mmol) in EtOH (150 mL) was added a solution of sodium hydroxide (20.0 g, 500 mmol) in water (120 mL). The reaction mixture was stirred at 90° C. for 16 h, then cooled to r.t. and extracted with DCM (4×200 mL). The combined organic fractions were washed with brine (100 mL), dried (Na$_2$SO$_4$), filtered and concentrated in vacuo to give the title compound (3.5 g, 83%) as a white solid. δ$_H$ (CDCl$_3$) 7.08 (1H, s), 6.40 (1H, s), 5.90 (2H, s), 3.80 (2H, br. s).

INTERMEDIATE 59 tert-Butyl (3S)-3-{[6-(trimethylsilyl)-5H-[1,3]dioxo[4,5-f]indol-7-yl]methyl}morpholine-4-carboxylate The title compound was prepared from Intermediate 25 and Intermediate 58 according to Method E and was isolated as a white foam (80%) after work up (EtOAc and water) and purification by column chromatography (SiO$_2$, 0-10% EtOAc/hexanes). LCMS (ES+) 433.0 (M+H)$^+$, RT 3.89 minutes (Method 4).

INTERMEDIATE 60

7-[(3S)-Morpholin-3-ylmethyl]-5H-[1,3]dioxolo[4,5-f]indole

The title compound was prepared from Intermediate 59 according to Method F and was isolated as a white foam (96%) after purification by column chromatography (SiO$_2$, 0-10% MeOH/DCM). LCMS (ES+) 261.0 (M+H)$^+$, RT 2.11 minutes (Method 4).

INTERMEDIATE 61

(3S)-3-(5H-[1,3]Dioxolo[4,5-f]indol-7-ylmethyl)morpholine-4-carbothioamide

The title compound was prepared from Intermediate 60 according to Method G and was isolated as an off-white solid (65%) that was used without further purification. LCMS (ES+) 320.0 (M+H)$^+$, RT 2.74 minutes (Method 4).

INTERMEDIATE 62

N-(2-Iodo-4,5-dimethoxyphenyl)acetamide

To a solution of N-(3,4-dimethoxyphenyl)acetamide (6.3 g, 32.0 mmol) in DCM (100 mL) and AcOH (6.5 mL) was added a solution of iodine monochloride (6.3 g, 39 mmol) in DCM (50 mL) dropwise. The reaction mixture was stirred at r.t. for 16 h. Aqueous sat. Na$_2$S$_2$O$_3$ (500 mL) was added. The organic fraction was separated, washed with water (2×250 mL), then brine (100 mL), dried (Na$_2$SO$_4$), filtered and concentrated in vacuo. Purification by column chromatography (SiO$_2$, 50% EtOAc/hexanes) gave the title compound (7.5 g, 72%) as a dark solid. LCMS (ES+) 321.8 (M+H)$^+$, RT 2.67 minutes (Method 4).

INTERMEDIATE 63

2-Iodo-4,5-dimethoxyaniline

A suspension of Intermediate 62 (7.0 g, 21.8 mmol) and NaOH (44.0 g, 1100 mmol) in EtOH (500 mL) and water (200 mL) was stirred at 100° C. for 3 h. The reaction mixture was cooled to r.t., then concentrated vacuo. CHCl$_3$ (300 mL) and water (300 mL) were added. The organic fraction was separated, washed with water (2×300 mL), dried (Na$_2$SO$_4$) and concentrated in vacuo to give the title compound (5.2 g, 84%) as a pale pink oil that was used without further purification. LCMS (ES+) 279.8 (M+H)$^+$, RT 2.95 minutes (Method 4).

INTERMEDIATE 64 tert-Butyl (3S)-3-{[5,6-dimethoxy-2-(trimethylsilyl)-1H-indol-3-yl]methyl}morpholine-4-carboxylate The title compound was prepared from Intermediate 25 and Intermediate 63 according to Method E and was isolated as a yellow oil (66%) after work up (EtOAc and water) and purification by column chromatography (SiO$_2$, 20-33% EtOAc/hexanes). $\delta_H$ (CDCl$_3$) 7.55 (1H, br. s), 7.40-7.10 (1H, m), 6.66 (1H, s), 4.18-3.99 (1H, m), 3.77 (3H, s), 3.74 (1H, br. s), 3.71 (3H, s), 3.62 (1H, d, J 7.3 Hz), 3.53 (1H, d, J 11.7 Hz), 3.36-3.07 (4H, m), 2.69 (1H, d, J 14.3 Hz), 1.26 (9H, s), 0.20 (9H, s).

INTERMEDIATE 65

5,6-Dimethoxy-3-[(3S)-morpholin-3-ylmethyl]-1H-indole

The title compound was prepared from Intermediate 64 according to Method F and was isolated as a yellow oil (25%) after purification by column chromatography (SiO$_2$, 0-20% MeOH/DCM). LCMS (ES+) 277.1 (M+H)$^+$, RT 2.03 minutes (Method 4).

INTERMEDIATE 66

2-Iodo-4-(methylsulfonyl)aniline

To a stirred suspension of 4-(methylsulfonyl)aniline hydrochloride (2.0 g, 9.7 mmol) in EtOH (40 mL) was added KO$^t$Bu (1.3 g, 11.4 mmol). The reaction mixture was stirred for 15 minutes, then a slurry of silver sulfate (3.3 g, 10.6 mmol) and iodine (2.4 g, 9.6 mmol) in EtOH (100 mL) was added. The reaction mixture was stirred at 50° C. for 3 h, then cooled to r.t., filtered through Celite®, and the filtrate concentrated in vacuo. Recrystallisation from EtOH gave the title compound (1.9 g, 66%) as an off white solid. LCMS (ES+) 319.8 (M+Na)$^+$, RT 2.77 minutes (Method 4).

INTERMEDIATE 67 tert-Butyl (3S)-3-{[5-(methylsulfonyl)-2-(trimethylsilyl)-1H-indol-3-yl]methyl}morpholine-4-carboxylate The title compound was prepared from Intermediate 25 and Intermediate 66 according to Method E and was isolated as a white foam (48%) after work-up (EtOAc and water) and purification by column chromatography (SiO$_2$, 0-33% EtOAc/hexanes). $\delta_H$ (CDCl$_3$) 8.71-8.30 (1H, br. s), 8.26 (1H, br. s), 7.75 (1H, d, J 8.8 Hz), 7.48 (1H, d, J 8.6 Hz), 4.31-4.20 (1H, m), 3.98-3.80 (2H, m), 3.69 (1H, d, J 11.4 Hz), 3.60-3.19 (5H, m), 3.12 (3H, s), 1.28 (9H, s), 0.47 (9H, s).

INTERMEDIATE 68

5-(Methylsulfonyl)-3-[(3S)-morpholin-3-ylmethyl]-1H-indole

The title compound was prepared from Intermediate 67 according to Method F and was isolated as an off-white foam (quantitative) that was used without further purification. LCMS (ES+) 295.0 (M+H)$^+$, RT 1.90 minutes (Method 4).

INTERMEDIATE 69

(3S)-3-{[5-(Methylsulfonyl)-1H-indol-3-yl]methyl}morpholine-4-carbothioamide

The title compound was prepared from Intermediate 68 according to Method G and was isolated as a white solid (58%) that was used without further purification. LCMS (ES+) 354.0 (M+H)$^+$, RT 2.54 minutes (Method 4).

INTERMEDIATE 70

2-Iodo-4-(1H-1,2,4-triazol-1-yl)aniline

To a stirred solution of 1-(4-aminophenyl)-1,2,4-triazole (1.0 g, 6.25 mmol) in MeOH (10 mL) and water (10 mL) was added CaCO$_3$ (1.2 g, 12.0 mmol), followed by a solution of iodine monochloride (1.2 g, 7.38 mmol) in MeOH (10 mL). The reaction mixture was stirred at r.t. for 1.5 h, and then partitioned between EtOAc (100 mL) and aqueous sat. Na$_2$S$_2$O$_3$ (100 mL). The organic fraction was separated, washed with aqueous sat. Na$_2$S$_2$O$_3$ (100 mL), then water (100 mL), brine (50 mL), dried (Na$_2$SO$_4$), filtered and concentrated in vacuo. Purification by column chromatography (SiO$_2$, 0-100% EtOAc/hexanes) gave the title compound (1.2 g, 67%). LCMS (ES+) 286.9 (M+H)$^+$, RT 2.78 minutes (Method 4).

INTERMEDIATE 71 tert-Butyl (3S)-3-{[5-(1H-1,2,4-triazol-1-yl)-2-(trimethylsilyl)-1H-indol-3-yl]methyl}morpholine-4-carboxylate The title compound was prepared from Intermediate 25 and Intermediate 70 according to Method E and was isolated as a yellow solid (44%) after work-up (EtOAc and water) and purification by column chromatography (SiO$_2$, 0-33% EtOAc/hexanes). LCMS (ES+) 498.2 (M+H)$^+$, RT 4.03 minutes (Method 4).

INTERMEDIATE 72

3-[(3S)-Morpholin-3-ylmethyl]-5-(1H-1,2,4-triazol-1-yl)-1H-indole

The title compound was prepared from Intermediate 71 according to Method F and was isolated as a pale yellow solid (78%) after trituration in Et$_2$O. LCMS (ES+) 284.0 (M+H)$^+$, RT 2.05 minutes (Method 4).

INTERMEDIATE 73

(3S)-3-{[5-(1H-1,2,4-Triazol-1-yl)-1H-indol-3-yl]methyl}morpholine-4-carbothioamide The title compound was prepared from Intermediate 72 according to Method G and was isolated as an off-white foam (quantitative) that was used without further purification. LCMS (ES+) 343.0 (M+H)$^+$, RT 2.53 minutes (Method 4).

INTERMEDIATE 74

7-Bromo-2,3-dihydrobenzo[1,4]oxazine-4-carbothioic acid amide

A mixture of 7-bromo-3,4-dihydro-2H-benzo[1,4]oxazine (7.07 g, 33.00 mmol) and 1,1'-thiocarbonyldiimidazole (8.86 g, 49.70 mmol) in THF (83 mL) was heated to 120° C. under microwave irradiation, in a sealed tube, for 20 minutes, and then cooled to r.t. NH$_3$ (110 mL, 7N solution in MeOH, 770 mmol) was added. The reaction mixture was stirred at r.t. for 16 h, and then concentrated in vacuo. The residue was triturated with 1M aqueous HCl, then Et$_2$O, water and again Et$_2$O, and then dried in vacuo to give the title compound (5.31 g, 59%) as a cream solid. $\delta_H$ (DMSO-d$_6$) 8.66-7.53 (2H, m), 7.39 (1H, d, J 8.7 Hz), 7.15 (1H, d, J 2.3 Hz), 7.07 (1H, dd, J 8.9 and 2.3 Hz), 4.30-4.20 (4H, m). LCMS (ES+) 272.9 and 274.9 (M+H)$^+$, RT 3.12 minutes (Method 7).

INTERMEDIATE 75

(3S)-3-[(5,6-Dimethoxy-1H-indol-3-yl)methyl]morpholine-4-carbothioamide

To a solution of Intermediate 65 (0.24 g, 0.87 mmol) in THF (10 mL) at r.t. was added 1,1'-thiocarbonyldiimidazole (0.240 g, 1.35 mmol) and the reaction mixture was stirred overnight. The reaction mixture was partitioned between EtOAc (50 mL) and water (20 mL), the organics were separated and washed with brine (20 mL), dried (Na$_2$SO$_4$), filtered and concentrated in vacuo. The crude material was re-dissolved in MeCN (10 mL) and aqueous ammonia (10 mL, 0.88 g/mL). The reaction mixture was heated at 60° C. overnight, then cooled and partitioned between EtOAc (50 mL) and water (50 mL). The aqueous was separated and extracted into EtOAc (2×20 mL), the combined organics were washed with brine (20 mL), dried (Na$_2$SO$_4$), filtered and concentrated in vacuo to give the title compound (110 mg, 38%) as a yellow foam, which was used as such. LCMS (ES+) 336.0 (M+H)$^+$, RT 2.57 minutes (Method 4).

EXAMPLE 1

2-[(3S)-3-(1H-Indol-3-ylmethyl)morpholin-4-yl]-4-methyl-1,3-thiazole-5-carboxamide To a stirred suspension of acetoacetamide (0.25 g, 2.48 mmol) in THF (5 mL) at 0° C. was added Br$_2$ (0.396 g, 0.128 mL, 2.48 mmol) dropwise. The reaction mixture was stirred for 2 minutes and Intermediate 5 (0.70 g, 2.48 mmol) and DIPEA (0.64 g, 0.90 mL, 4.95 mmol) were added. After stirring at 95° C. for 2 h, the reaction mixture was cooled to r.t. and poured into brine (5 mL) and the aqueous layer was extracted with EtOAc (2×5 mL). The combined organic fractions were concentrated in vacuo. The residue was triturated with Et$_2$O to give the title compound (0.30 g, 34%) as a yellow solid. $\delta_H$ (CDCl$_3$) 8.08 (1H, br. s), 7.97 (1H, d, J 7.4 Hz), 7.41-7.38 (1H, m), 7.27-7.16 (2H, m), 7.13 (1H, d, J 2.2 Hz), 4.22-4.04 (2H, m), 3.90 (1H, d, J 11.7 Hz), 3.72-3.62 (3H, m), 3.60-3.47 (1H, m), 3.43-3.38 (1H, m), 3.06 (1H, dd, J 13.8 Hz and J 4.0 Hz), 2.62 (3H, s). LCMS (ES+) 357.0 (M+H)$^+$, RT 2.63 minutes (Method 4).

EXAMPLE 2

N-Cyclopropyl-2-[(3S)-3-(1H-indol-3-ylmethyl)morpholin-4-yl]-4-methyl-1,3-thiazole-5-carboxamide To a stirred solution of Intermediate 8 (0.53 g, 2.85 mmol) in IPA (10 mL) was added DIPEA (0.08 mL, 0.44 mmol) followed by Intermediate 4 (0.10 g, 0.44 mmol). The reaction mixture was heated at 120° C. under microwave irradiation for 40 minutes, cooled to r.t. and then concentrated in vacuo. Purification by preparative HPLC (Method 5) gave the title compound (0.023 g, 13%) as a brown solid. $\delta_H$ (DMSO-d$_6$) 10.90 (1H, br. s), 7.84 (1H, d, J 7.9 Hz), 7.73 (1H, d, J 3.6 Hz), 7.35 (1H, d, J 7.9 Hz), 7.19 (1H, d, J 2.1 Hz), 7.05 (2H, m), 4.09 (1H, m), 3.97 (1H, d, J 8.5 Hz), 3.70 (1H, m), 3.51-3.29 (3H, m), 3.17 (2H, s), 2.84 (1H, m), 2.72 (1H, m), 2.44 (3H, s), 0.65 (2H, m), 0.51 (2H, m). LCMS (ES+) 397.0 (M+H)$^+$, RT 3.02 minutes (Method 1).

EXAMPLE 3

Method H

1-{2-[(3S)-3-(1H-Indol-3-ylmethyl)morpholin-4-yl]-4-methyl-1,3-thiazol-5-yl}ethanone To a stirred solution of 3-chloro-2,4-pentanedione (0.048 mL, 0.40 mmol) and Intermediate 5 (0.10 g, 0.36 mmol) in THF (5 mL) was added DIPEA (0.095 mL, 0.55 mmol). The reaction mixture was stirred at 65° C. for 1.5 h, then cooled to r.t. and DCM (10 mL) and water (10 mL) were added. The aqueous layer was extracted with DCM (2×10 mL). The combined organic fractions were washed with water (3×15 mL), dried (Na$_2$SO$_4$), filtered and the solvent evaporated in vacuo. The residue was purified by column chromatography (SiO$_2$, 0-30% EtOAc/DCM) to give the title compound (0.073 g, 57%) as an off-white solid. $\delta_H$ (DMSO-d$_6$) 10.88 (1H, s), 7.81 (1H, d, J 7.7 Hz), 7.35 (1H, d, J 7.7 Hz), 7.19 (1H, d, J 2.3 Hz), 7.12-6.98 (2H, m), 4.25-4.13 (1H, m), 3.98 (1H, d, J 7.7 Hz), 3.80-3.40 (5H, m), 3.37-3.21 (1H, m), 2.91 (1H, dd, J 13.8 Hz and J 4.5 Hz), 2.53 (3H, s), 2.38 (3H, s). LCMS (ES+) 356.0 (M+H)$^+$, RT 2.91 minutes (Method 2).

EXAMPLE 4

4-Methyl-2-[(3S)-3-{[5-(trifluoromethoxy)-1H-indol-3-yl]methyl}morpholin-4-yl]-1,3-thiazole-5-carboxamide The title compound was prepared from Intermediate 9 and Intermediate 36 according to Method H and was isolated as a white solid (19%) after purification by preparative HPLC (Method 6). $\delta_H$ (DMSO-d$_6$) 11.17 (1H, s), 7.93 (1H, s), 7.43 (1H, d, J 8.7 Hz), 7.34 (1H, d, J 1.9 Hz), 7.10-7.02 (3H, m), 4.27-4.14 (1H, m), 4.05-3.92 (1H, m), 3.69 (1H, d, J 11.5 Hz), 3.62-3.36 (5H, m), 2.84 (1H, dd, J 13.6 Hz and J 3.0 Hz), 2.48 (3H, s). LCMS (ES+) 441.0 (M+H)$^+$, RT 2.76 minutes (Method 2).

EXAMPLE 5

Methyl 3-{[(3S)-4-(5-carbamoyl-4-methyl-1,3-thiazol-2-yl)morpholin-3-yl]methyl}-1H-indole-5-carboxylate The title compound was prepared from Intermediate 9 and Intermediate 28 according to Method H and was isolated as a white solid (26%) after purification by preparative HPLC (Method 6). $\delta_H$ (DMSO-d$_6$) 11.32 (1H, s), 8.56 (1H, s), 7.74 (1H, dd, J 8.7 Hz and J 1.5 Hz), 7.43 (1H, d, J 8.7 Hz), 7.33 (1H, d, J 1.9 Hz), 7.06 (2H, s), 4.25-4.12 (1H, m), 4.06-3.93 (1H, m), 3.85 (3H, s), 3.70 (1H, d, J 11.7 Hz), 3.62-3.40 (4H, m), 3.39-3.18 (1H, m), 2.93 (1H, dd, J 13.8 Hz and J 4.0 Hz), 2.52 (3H, s). LCMS (ES+) 415.0 (M+H)$^+$, RT 2.45 minutes (Method 2).

EXAMPLE 6

Methyl 3-{[(3S)-4-(5-acetyl-4-methyl-1,3-thiazol-2-yl)morpholin-3-yl]methyl}-1H-indole-5-carboxylate The title compound was prepared from 3-chloro-2,4-pentanedione and Intermediate 28 according to Method H and was isolated as a white solid (33%) after purification by column chromatography (SiO$_2$, 0-30% EtOAc/DCM). $\delta_H$ (DMSO-d$_6$) 11.30 (1H, s), 8.55 (1H, d, J 1.3 Hz), 7.74 (1H, dd, J 8.7 Hz and J 1.7 Hz), 7.43 (1H, dd, J 8.7 Hz and J 0.4 Hz), 7.33 (1H, d, J 2.1 Hz), 4.35-4.19 (1H, m), 4.02-3.94 (1H, m), 3.86 (3H, s), 3.73 (1H, d, J 11.7 Hz), 3.65-3.41 (4H, m), 3.39-3.24 (1H, m), 2.97 (1H, dd, J 13.8 Hz and J 4.5 Hz), 2.56 (3H, s), 2.39 (3H, s). LCMS (ES+) 414.0 (M+H)$^+$, RT 2.85 minutes (Method 2).

EXAMPLE 7

Methyl 3-{[(3S)-4-(5-acetyl-4-methyl-1,3-thiazol-2-yl)morpholin-3-yl]methyl}-1H-indole-6-carboxylate The title compound was prepared from 3-chloro-2,4-pentanedione and Intermediate 31 according to Method H and was isolated as a white solid (36%) after purification by column chromatography (SiO$_2$, 20% EtOAc/DCM). $\delta_H$ (CD$_3$OD) 8.08 (1H, dd, J 1.5 Hz and J 0.6 Hz), 7.92 (1H, d, J 8.5 Hz), 7.74 (1H, dd, J 8.5 Hz and J 1.5 Hz), 7.35 (1H, s), 4.40-4.28 (1H, m), 4.11-4.04 (1H, m), 3.93 (3H, s), 3.88 (1H, d, J 11.7 Hz), 3.73-3.54 (4H, m), 3.45-3.38 (1H, m), 3.18-3.07 (1H, m), 2.53 (3H, s), 2.40 (3H, s). Exchangeable proton not observed. LCMS (ES+) 414.0 (M+H)$^+$, RT 2.94 minutes (Method 2).

EXAMPLE 8

1-(2-{(3R)-3-[(3-Bromophenoxy)methyl]morpholin-4-yl}-4-methyl-1,3-thiazol-5-yl)ethanone The title compound was prepared from 3-chloro-2,4-pentanedione and Intermediate 22 according to Method H and was isolated as a white solid (70%) after purification by column chromatography (SiO$_2$, 0-5% EtOAc/DCM). $\delta_H$ (DMSO-d$_6$) 7.29-7.20 (2H, m), 7.17-7.11 (1H, m), 7.00 (1H, ddd, J 8.3 Hz, J 2.4 Hz and J 0.9 Hz), 4.44-4.31 (2H, m), 4.26-4.13 (1H, m), 4.00 (1H, d, J 11.9 Hz), 3.96-3.89 (1H, m), 3.71-3.45 (4H, m), 2.48 (3H, s), 2.39 (3H, s). LCMS (ES+) 413.0 (M+H)$^+$, RT 3.23 minutes (Method 2).

EXAMPLE 9

1-{2-[(3S)-3-(3-Bromobenzyl)morpholin-4-yl]-4-methyl-1,3-thiazol-5-yl}ethanone

The title compound was prepared from 3-chloro-2,4-pentanedione and Intermediate 21 according to Method H and was isolated as a white solid (43%) after purification by column chromatography (SiO$_2$, 0-100% DCM/hexanes). $\delta_H$ (DMSO-d$_6$) 7.48 (1H, d, J 1.6 Hz), 7.40-7.36 (1H, m), 7.33-7.20 (2H, m), 4.25-4.12 (1H, m), 3.99-3.90 (1H, m), 3.70-3.43 (5H, m), 3.03 (2H, d, J 7.5 Hz), 2.43 (3H, s), 2.35 (3H, s). LCMS (ES+) 397.0 (M+H)$^+$, RT 3.19 minutes (Method 2).

EXAMPLE 10

2-[(3S)-3-(3-Bromobenzyl)morpholin-4-yl]-4-methyl-1,3-thiazole-5-carboxamide

The title compound was prepared from Intermediate 9 and Intermediate 21 according to Method H and was isolated as a white solid (75%) after purification by column chromatography (SiO$_2$, EtOAc). $\delta_H$ (DMSO-d$_6$) 7.48 (1H, d, J 0.6 Hz), 7.44-7.35 (1H, m), 7.33-7.19 (2H, m), 7.10-7.00 (2H, m), 4.15-3.84 (2H, m), 3.71-3.41 (5H, m), 3.16-3.01 (1H, m), 2.99-2.86 (1H, m), 2.38 (3H, s). LCMS (ES+) 398.0 (M+H)$^+$, RT 3.06 minutes (Method 4).

EXAMPLE 11

3-{[(3S)-4-(5-Acetyl-4-methyl-1,3-thiazol-2-yl)morpholin-3-yl]methyl}-1H-indole-5-carboxylic acid To a stirred solution of Example 6 (0.180 g, 0.44 mmol) in dioxane (3 mL) was added lithium hydroxide monohydrate (0.037 g, 0.87 mmol) in water (3 mL). The reaction mixture was stirred at 60° C. for 16 h. The reaction mixture was concentrated in vacuo. DCM (5 mL) and water (5 mL) were added. The aqueous layer was washed with DCM (2×3 mL), then acidified with aqueous HCl (2N, 5 mL) and extracted with EtOAc (2×5 mL). The combined organic fractions were dried (Na$_2$SO$_4$), filtered and the solvent evaporated in vacuo to give the title compound (0.127 g, 73%) as a pale yellow solid that required no purification. $\delta_H$ (DMSO-d$_6$) 12.40 (1H, s), 11.26 (1H, s), 8.56 (1H, s), 7.73 (1H, dd, J 8.6 Hz and J 1.3 Hz), 7.40 (1H, d, J 8.6 Hz), 7.32 (1H, d, J 1.8 Hz), 4.36-4.20 (1H, m), 4.02-3.95 (1H, m), 3.73 (1H, d, J 11.6 Hz), 3.67-3.42 (4H, m), 3.38-3.26 (1H, m), 2.96 (1H, dd, J 13.6 Hz and J 4.3 Hz), 2.55 (3H, s), 2.38 (3H, s). LCMS (ES+) 400.0 (M+H)$^+$, RT 2.47 minutes (Method 2).

EXAMPLE 12

3-{[(3S)-4-(5-Acetyl-4-methyl-1,3-thiazol-2-yl)morpholin-3-yl]methyl}-N,N-dimethyl-1H-indole-5-carboxamide To a stirred solution of Example 11 (0.115 g, 0.29 mmol) in DMF (2 mL) was added pentafluorophenol (0.064 g, 0.35 mmol), DIPEA (0.100 mL, 0.57 mmol) and EDC (0.072 g, 0.37 mmol). The reaction mixture was stirred at r.t. for 48 h. Dimethylamine (40% w/v in water, 5 mL) was added and the reaction mixture stirred for 16 h at r.t. The reaction mixture was concentrated in vacuo. DCM (5 mL) and water (5 mL) were added. The aqueous layer was extracted with DCM (2×3 mL). The combined organic fractions were washed with water (3×15 mL), dried (Na$_2$SO$_4$), filtered and the solvent evaporated in vacuo. The residue was purified by preparative HPLC (Method 6) to give the title compound (0.040 g, 45%) as a white solid. $\delta_H$ (CD$_3$OD) 8.07 (1H, s), 7.42 (1H, m), 7.25-7.19 (2H, m), 4.39-4.29 (1H, m), 4.14-3.99 (1H, m), 3.88 (1H, d, J 11.9 Hz), 3.72-3.51 (4H, m), 3.42 (1H, dd, J 13.8 Hz and J 10.2 Hz), 3.19-3.03 (7H, m), 2.57 (3H, s), 2.43 (3H, s). Exchangeable proton not observed. LCMS (ES+) 427.0 (M+H)$^+$, RT 2.59 minutes (Method 2).

EXAMPLE 13

1-(4-Methyl-2-{(3S)-3-[3-(pyridin-4-ylamino)benzyl]morpholin-4-yl}-1,3-thiazol-5-yl)ethanone A flask was charged with Example 9 (0.100 g, 0.25 mmol), Pd$_2$dba$_3$ (0.0046 g, 0.005 mmol), X-Phos (0.012 g, 0.025 mmol), 4-aminopyridine (0.026 g, 0.28 mmol) and sodium tert-butoxide (0.061 g, 0.63 mmol). tert-BuOH (10 mL) was then added. The reaction mixture was stirred for 16 h at 95° C. The solvent was evaporated in vacuo and DCM (10 mL) and water (10 mL) were added. The aqueous layer was extracted with DCM (2×10 mL). The combined organic layers were washed with water (3×10 mL), dried (Na$_2$SO$_4$), filtered and the solvent evaporated in vacuo. The residue was purified by column chromatography (SiO$_2$, 1:100 MeOH/DCM) to give the title compound (0.022 g, 22%) as a white solid. δ$_H$ (DMSO-d$_6$) 8.82 (1H, s), 8.18 (2H, dd, J 4.9 Hz and J 1.3 Hz), 7.27 (1H, t, J 7.7 Hz), 7.13 (1H, s), 7.02 (1H, dd, J 8.1 Hz and J 1.3 Hz), 6.94 (1H, d, J 7.5 Hz), 6.88 (2H, dd, J 4.7 Hz and J 1.5 Hz), 4.11-4.03 (1H, m), 3.96 (1H, d, J 7.7 Hz), 3.84-3.66 (2H, m), 3.63-3.46 (3H, m), 3.06 (1H, dd, J 13.2 Hz and J 8.5 Hz), 2.96 (1H, dd, J 13.2 Hz and J 6.6 Hz), 2.42 (3H, s), 2.34 (3H, s). LCMS (ES+) 409.0 (M+H)$^+$, RT 2.67 minutes (Method 3).

EXAMPLE 14

1-{2-[(3S)-3-(3-Anilinobenzyl)morpholin-4-yl]-4-methyl-1,3-thiazol-5-yl}ethanone A flask was charged with Example 9 (0.100 g, 0.25 mmol), Pd$_2$dba$_3$ (0.0046 g, 0.005 mmol), X-Phos (0.012 g, 0.025 mmol), aniline (0.032 mL, 0.28 mmol) and sodium tert-butoxide (0.061 g, 0.63 mmol). tert-BuOH (10 mL) was then added. The reaction was stirred for 18 h at 90° C. The solvent was evaporated in vacuo and DCM (10 mL) and water (10 mL) were added. The aqueous layer was extracted with DCM (2×10 mL). The combined organic fractions were washed with water (3×10 mL), dried (Na$_2$SO$_4$), filtered and the solvent evaporated in vacuo. The residue was purified by column chromatography (SiO$_2$, DCM) to give the title compound (0.038 g, 37%) as a white solid. δ$_H$ (DMSO-d$_6$) 8.21 (1H, s), 7.36-7.21 (3H, m), 7.18-7.08 (3H, m), 7.02-6.96 (1H, m), 6.95-6.87 (1H, m), 6.81 (1H, d, J 7.5 Hz), 4.16-3.97 (2H, m), 3.91-3.82 (1H, m), 3.79 (1H, d, J 11.7 Hz), 3.67-3.54 (3H, m), 3.11 (1H, dd, J 13.2 Hz and J 9.2 Hz), 2.93 (1H, dd, J 12.8 Hz and J 5.5 Hz), 2.54 (3H, s), 2.44 (3H, s). LCMS (ES+) 408.0 (M+H)$^+$, RT 3.29 minutes (Method 2).

EXAMPLE 15

1-(4-Methyl-2-{(3S)-3-[3-(pyridin-3-yl)benzyl]morpholin-4-yl}-1,3-thiazol-5-yl)-ethanone A flask was charged with Example 9 (0.100 g, 0.25 mmol), pyridine-3-boronic acid (0.050 g, 0.38 mmol), [1,1'-bis(diphenylphosphino)ferrocene]dichloropalladium(II) (0.010 g, 0.010 mmol) and cesium carbonate (0.165 g, 0.51 mmol). DME (2.5 mL) and water (0.5 mL) were then added. The reaction mixture was stirred for 16 h at 90° C. The solvent was evaporated in vacuo and DCM (10 mL) and water (10 mL) were added. The aqueous layer was extracted with DCM (2×10 mL). The combined organic fractions were washed with water (3×10 mL), dried (Na$_2$SO$_4$), filtered and the solvent evaporated in vacuo. The residue was purified by column chromatography (SiO$_2$, 20% EtOAc/DCM) to give the title compound (0.027 g, 28%) as a white solid. δ$_H$ (DMSO-d$_6$) 8.84 (1H, dd, J 2.3 Hz and J 0.8 Hz), 8.57 (1H, dd, J 4.7 Hz and J 1.5 Hz), 8.01 (1H, ddd, J 8.1 Hz, J 2.4 Hz and J 1.7 Hz), 7.63-7.57 (1H, m), 7.57-7.45 (2H, m), 7.42 (1H, t, J 7.5 Hz), 7.37-7.29 (1H, m), 4.28-4.18 (1H, m), 3.97 (1H, d, J 8.5 Hz), 3.75 (2H, m), 3.68-3.47 (3H, m), 3.13 (2H, d, J 7.3 Hz), 2.39 (3H, s), 2.31 (3H, s). LCMS (ES+) 394.0 (M+H)$^+$, RT 2.79 minutes (Method 2).

EXAMPLE 16

1-[2-(6-Bromo-2,3-dihydro-4H-benzo[1,4]oxazin-4-yl)-4-methyl-1,3-thiazol-5-yl]-ethanone The title compound was prepared from 3-chloro-2,4-pentanedione and Intermediate 39 according to Method H and was isolated as light beige crystals (39%) after recrystallisation from MeCN and a few drops of DMSO. δ$_H$ (DMSO-d$_6$) 8.48 (1H, d, J 2.3 Hz), 7.23 (1H, dd, J 8.7 Hz and J 2.3 Hz), 6.94 (1H, d, J 8.7 Hz), 4.36-4.28 (2H, m), 4.08-3.98 (2H, m), 2.59 (3H, s), 2.47 (3H, s). LCMS (ES+) 355.0 (M+H)$^+$, RT 3.37 minutes (Method 2).

EXAMPLE 17

3-{[(3S)-4-(5-Acetyl-4-methyl-1,3-thiazol-2-yl)morpholin-3-yl]methyl}-1H-indole-5-carbonitrile The title compound was prepared from 3-chloro-2,4-pentanedione and Intermediate 42 according to Method H and was isolated as a white solid (52%) after trituration with DCM. δ$_H$ (DMSO-d$_6$) 11.47 (1H, s), 8.45 (1H, s), 7.54-7.48 (1H, m), 7.46-7.40 (2H, m), 4.39-4.29 (1H, m), 4.02-3.95 (1H, m), 3.75-3.68 (1H, m), 3.61-3.46 (4H, m), 3.24-3.31 (1H, m), 2.97 (1H, dd, J 13.9 and 4.8 Hz), 2.54 (3H, s), 2.37 (3H, s). LCMS (ES+) 381.0 (M+H)$^+$, RT 3.21 minutes (Method 4).

EXAMPLE 18

1-(2-{(3S)-3-[(6-Methoxy-1H-indol-3-yl)methyl]morpholin-4-yl}-4-methyl-1,3-thiazol-5-yl)ethanone The title compound was prepared from 3-chloro-2,4-pentanedione and Intermediate 45 according to Method H and was isolated as a white solid (7%) after purification by column chromatography (SiO$_2$, 10-15% EtOAc/hexanes), followed by preparative HPLC (Method 6). δ$_H$ (DMSO-d$_6$) 10.68 (1H, s), 7.67 (1H, d, J 8.7 Hz), 7.05 (1H, s), 6.85 (1H, d, J 2.1 Hz), 6.69 (1H, dd, J 8.6 and 2.1 Hz), 4.22-4.12 (1H, m), 3.97 (1H, d, J 7.2 Hz), 3.76 (3H, s), 3.72 (1H, d, J 11.7 Hz), 3.53 (2H, d, J 8.5 Hz), 3.47 (1H, d, J 8.6 Hz), 3.40-3.20 (2H, m), 2.86 (1H, dd, J 14.0 and 4.3 Hz), 2.53 (3H, s), 2.39 (3H, s). LCMS (ES+) 386.0 (M+H)$^+$, RT 3.27 minutes (Method 4).

EXAMPLE 19

1-(2-{(3S)-3-[(5-Acetyl-1H-indol-3-yl)methyl]morpholin-4-yl}-4-methyl-1,3-thiazol-5-yl)ethanone The title compound was prepared from 3-chloro-2,4-pentanedione and Intermediate 49 according to Method H and was isolated as a pale yellow solid (13%) after purification by column chromatography (SiO$_2$, 80-100% EtOAc/hexanes), followed by trituration with Et$_2$O. δ$_H$ (DMSO-d$_6$) 11.30 (1H, s), 8.47 (1H, s), 7.74 (1H, dd, J 8.6 and 1.3 Hz), 7.42 (1H, d, J 8.3 Hz), 7.34 (1H, d, J 1.8 Hz), 4.31-4.18 (1H, m), 4.02-3.96 (1H, m), 3.78-3.68 (2H, m), 3.62-3.46 (3H, m), 3.30-3.27 (4H, m), 3.02 (1H, dd, J 14.1 and 5.1 Hz), 2.63 (3H, s), 2.37 (3H, s). LCMS (ES+) 398.0 (M+H)$^+$, 420.0 (M+Na)$^+$, RT 3.09 minutes (Method 4).

EXAMPLE 20

1-(2-{(3S)-3-[(2,2-Difluoro-5H-[1,3]dioxolo[4,5-f]indol-7-yl)methyl]morpholin-4-yl}-4-methyl-1,3-thiazol-5-yl)ethanone The title compound was prepared from 3-chloro-2,4-pentanedione and Intermediate 52 according to Method H and was isolated as a white solid (59%) after purification by column chromatography (SiO$_2$, 0-5% MeOH/DCM, followed by SiO$_2$, 25-75% EtOAc/hexanes). $\delta_H$ (CD$_3$OD) 7.69 (1H, s), 7.17-7.11 (2H, m), 4.40-4.31 (1H, m), 4.10-4.03 (1H, m), 3.91-3.83 (1H, m), 3.73-3.50 (4H, m), 3.33-3.29 (1H, m), 3.08-2.98 (1H, m), 2.58 (3H, s), 2.42 (3H, s). Exchangeable proton was not observed. LCMS (ES+) 436.1 (M+H)$^+$, RT 2.93 minutes (Method 2).

EXAMPLE 21

1-(3-{[(3S)-4-(5-Acetyl-4-methyl-1,3-thiazol-2-yl)morpholin-3-yl]methyl}-1H-indol-5-yl)-2,2,2-trifluoroethanone The title compound was prepared from 3-chloro-2,4-pentanedione and Intermediate 56 according to Method H and was isolated as a yellow solid (85%) after purification by column chromatography (SiO$_2$, 50-70% EtOAc/hexanes). $\delta_H$ (CD$_3$OD) Mixture of ketone and hydrate forms: 8.71-8.63 and 8.21-8.15 (1H, s), 7.91-7.83 and 7.54-7.47 (1H, m), 7.37 (1H, s), 7.33 and 7.18 (1H, m), 4.45-4.24 (1H, m), 4.13-4.03 (1H, m), 3.96-3.84 (1H, m), 3.81-3.49 (4H, m), 3.27-3.06 (2H, m), 2.58 and 2.53 (3H, s), 2.46-2.39 (3H, m). Exchangeable proton was not observed. LCMS (ES+) 452.2 (M+H)$^+$, RT 2.87 minutes (Method 3).

EXAMPLE 22

1-{2-[(3S)-3-(5H-[1,3]Dioxolo[4,5-f]indol-7-ylmethyl)morpholin-4-yl]-4-methyl-1,3-thiazol-5-yl}ethanone The title compound was prepared from 3-chloro-2,4-pentanedione and Intermediate 61 according to Method H and was isolated as a white solid (42%) after trituration with Et$_2$O. $\delta_H$ (DMSO-d$_6$) 10.68 (1H, br. s), 7.36 (1H, br. s), 7.02 (1H, d, J 1.8 Hz), 6.86 (1H, s), 5.97-5.89 (2H, m), 4.27-4.11 (1H, m), 3.97 (1H, d, J 6.8 Hz), 3.71 (1H, d, J 11.6 Hz), 3.66-3.42 (4H, m), 3.20 (1H, J 13.9 and 10.9 Hz), 2.78 (1H, J 13.6 and 3.5 Hz), 2.55 (3H, s), 2.39 (3H, s). LCMS (ES+) 400.0 (M+H)$^+$, RT 3.20 minutes (Method 4).

EXAMPLE 23

1-(2-{(3S)-3-[(5,6-Dimethoxy-1H-indol-3-yl)methyl]morpholin-4-yl}-4-methyl-1,3-thiazol-5-yl)ethanone The title compound was prepared from 3-chloro-2,4-pentanedione and Intermediate 75 according to Method H and was isolated as a white solid (67%) after purification by column chromatography (SiO$_2$, EtOAc). $\delta_H$ (CDCl$_3$) 7.90 (1H, br. s), 7.37 (1H, s), 7.02 (1H, s), 6.91 (1H, s), 4.20-4.10 (1H, m), 4.10-4.04 (1H, m), 4.04 (3H, s), 3.94 (3H, s), 3.94-3.82 (2H, m), 3.72-3.37 (4H, m), 3.05-2.96 (1H, m), 2.62 (3H, s) 2.47 (3H, s). LCMS (ES+) 416.0 (M+H)$^+$, RT 3.05 minutes (Method 4).

EXAMPLE 24

1-{4-Methyl-2-[(3S)-3-{[5-(methylsulfonyl)-1H-indol-3-yl]methyl}morpholin-4-yl]-1,3-thiazol-5-yl}ethanone The title compound was prepared from 3-chloro-2,4-pentanedione and Intermediate 69 according to Method H and was isolated as a white solid (67%) after purification by column chromatography (SiO$_2$, EtOAc). $\delta_H$ (DMSO-d$_6$) 11.48 (1H, d, J 1.0 Hz), 8.41 (1H, d, J 1.0 Hz), 7.62 (1H, dd, J 8.6 and 1.8 Hz), 7.56 (1H, d, J 8.6 Hz), 7.45 (1H, d, J 2.0 Hz), 4.37-4.25 (1H, m), 3.99 (1H, d, J 7.8 Hz), 3.75 (1H, d, J 11.6 Hz), 3.70-3.46 (1H, m), 3.37-3.27 (4H, m), 3.16 (3H, s), 3.04 (1H, dd, J 14.1 and 5.1 Hz), 2.50 (3H, s), 2.36 (3H, s). LCMS (ES+) 434.0 (M+H)$^+$, RT 2.88 minutes (Method 4).

EXAMPLE 25

1-{4-Methyl-2-[(3S)-3-{[5-(1H-1,2,4-triazol-1-yl)-1H-indol-3-yl]methyl}morpholin-4-yl]-1,3-thiazol-5-yl}ethanone The title compound was prepared from 3-chloro-2,4-pentanedione and Intermediate 73 according to Method H and was isolated as a white solid (36%) after purification by column chromatography (SiO$_2$, 0-100% EtOAc/hexanes), followed by preparative HPLC (Method 6). $\delta_H$ (DMSO-d$_6$) 11.19 (1H, d, J 1.3 Hz), 9.12 (1H, s), 8.20 (1H, s), 8.19 (1H, s), 7.55-7.46 (2H, m), 7.36 (1H, d, J 2.3 Hz), 4.35-4.24 (1H, m), 4.03-3.94 (1H, m), 3.75 (1H, d, J 11.6 Hz), 3.70-3.45 (4H, m), 3.37-3.25 (1H, m), 2.99 (1H, dd, J 13.9 and 4.8 Hz), 2.44 (3H, s), 2.36 (3H, s). LCMS (ES+) 423.1 (M+H)$^+$, RT 2.37 minutes (Method 2).

EXAMPLE 26

1-(4-Methyl-2-{7-[N-methyl-N-(1-methylpiperidin-4-yl)amino]-2,3-dihydro-4H-1,4-benzoxazin-4-yl}-1,3-thiazol-5-yl)ethanone To a stirred solution of Intermediate 74 (1.00 g, 3.66 mmol) in THF (20 mL) were added 2,6-lutidine (0.51 mL, 4.39 mmol) and 3-chloro-2,4-pentanedione (0.70 mL, 5.86 mmol). The reaction mixture was heated to 125° C. under microwave irradiation, in a sealed tube, for 20 minutes, and then partitioned between DCM (150 mL) and water (150 mL). The organic fraction was washed with sat. NaHCO$_3$ solution (150 mL), dried (NaSO$_4$), filtered, concentrated in vacuo, and the residue was purified by column chromatography (SiO$_2$, 0-4% MeOH/DCM). A mixture of this intermediate (0.15 g, 0.43 mmol), 1,2,3,4,5-pentaphenyl-1'-(di-tert-butylphosphino)ferrocene (0.006 g, 0.0085 mmol), Pd$_2$dba$_3$ (0.004 g, 0.0043 mmol), sodium tert-butoxide (0.047 g, 0.49 mmol) and 4-amino-1-methylpiperidine (0.145 g, 1.28 mmol) in toluene (2 mL) was heated to 100° C. for 20 h. The reaction mixture was then partitioned between DCM (5 mL) and water (5 mL). The organic fraction was dried (NaSO$_4$), filtered, concentrated in vacuo, and the residue was purified by preparative HPLC (Method 5). To a stirred solution of this intermediate (0.057 g, 0.15 mmol) in acetic acid (1 mL) was added formaldehyde (0.055 mL, 37% in water, 0.74 mmol). The reaction mixture was stirred for 5 minutes at r.t. before addition of sodium triacetoxyborohydride (0.062 g, 0.29 mmol). The reaction mixture was stirred for 1 h at r.t. Water (20 mL) was then added and the pH of the mixture adjusted to pH 10 with 2M aqueous NaOH solution. The aqueous fraction was separated and extracted with DCM (2×100 mL). The combined organic fractions were dried (NaSO$_4$), filtered, concentrated in vacuo and the residue purified by preparative HPLC (Method 9). The residue was dissolved in DCM (2 mL) and treated with 10% aqueous K$_2$CO$_3$ solution (4 mL). The mixture was stirred at r.t. for 10 minutes, then passed through a hydrophobic frit. The organic fraction was concentrated in vacuo to give the title compound (0.019 g, 7%) as a yellow oil. $\delta_H$ (DMSO-d$_6$) 7.64 (1H, d, J 9.0 Hz), 6.46 (1H, dd, J 9.0 and 2.8 Hz), 6.30 (1H, d, J 2.6 Hz), 4.26-4.20 (2H, m), 4.09-4.03

(2H, m), 3.59-3.47 (1H, m), 2.86-2.78 (2H, m), 2.69 (3H, s), 2.53 (3H, s), 2.40 (3H, s), 2.17 (3H, s), 2.06-1.95 (2H, m), 1.80-1.63 (2H, m), 1.59-1.49 (2H, m). LCMS (ES+) 401.2 (M+H)$^+$, RT 2.02 minutes (Method 7).

EXAMPLE 27

1-(4-Methyl-2-{6-[3-(piperidin-1-ylmethyl)phenyl]-2,3-dihydro-4H-1,4-benzoxazin-4-yl}-1,3-thiazol-5-yl)ethanone, acetic acid salt A mixture of Example 16 (0.15 g, 0.43 mmol), 3-(piperidin-1-ylmethyl)-phenylboronic acid pinacol ester hydrochloride (0.14 g, 0.43 mmol), tetrakis(triphenyl-phosphine)palladium(0) (0.015 g, 0.013 mmol) and Na$_2$CO$_3$ (0.71 mL, 2M in water, 1.41 mmol) in DME (2 mL) was heated under microwave irradiation at 120° C., in a sealed tube, for 20 minutes, then at 130° C. for 40 minutes. The reaction mixture was then cooled to r.t. and partitioned between EtOAc (50 mL) and water (50 mL). The organic fraction was dried (NaSO$_4$), filtered and concentrated in vacuo. Purification by preparative HPLC (Method 9) gave the title compound (0.028 g, 13%) as a clear oil. $\delta_H$ (DMSO-d$_6$) 8.40 (1H, d, J 2.1 Hz), 7.56-7.46 (2H, m), 7.44-7.36 (2H, m), 7.25 (1H, d, J 7.3 Hz), 7.06 (1H, d, J 8.5 Hz), 4.39-4.31 (2H, m), 4.16-4.10 (2H, m), 3.48 (2H, s), 2.59 (3H, s), 2.45 (2H, s), 2.39-2.30 (2H, m), 1.87 (3H, s), 1.55-1.44 (4H, m), 1.43-1.33 (2H, m). LCMS (ES+) 448.2 (M+H)$^+$, RT 3.22 minutes (Method 8).

EXAMPLE 28

2-(7-Bromo-2,3-dihydro-4H-1,4-benzoxazin-4-yl)-4-methyl-1,3-thiazole-5-carboxylic acid To a stirred mixture of methyl 2-chloroacetoacetate (1.29 g, 8.05 mmol) and 2,6-lutidine (0.86 g, 8.05 mmol) in THF (15 mL) was added a solution of Intermediate 74 (2.0 g, 7.32 mmol) in THF (15 mL) dropwise. The reaction mixture was stirred at r.t. for 16 h, then heated at reflux for 4 h. Additional portions of methyl 2-chloroacetoacetate (1.06 g, 7.04 mmol) and 2,6-lutidine (0.31 g, 2.93 mmol) were added. Heating was continued for 16 h before addition of water (200 mL) portionwise. The precipitate formed was filtered, washed with water, dried in vacuo and then suspended in a mixture of water (100 mL) and MeOH (50 mL). NaOH (0.54 g, 13.5 mmol) was added and the reaction mixture heated to reflux for 1 h. DME (20 mL) was added and heating was continued for 30 minutes. The reaction mixture was then allowed to cool to r.t. The aqueous phase was separated, diluted with water to 400 mL, and the solution was adjusted to pH 1 with 2M aqueous HCl. The precipitate formed was filtered, washed with water and dried in vacuo to give the title compound (1.77 g, 68%) as a white solid. $\delta_H$ (DMSO-d$_6$) 13.01-12.72 (1H, br. s), 8.12 (1H, d, J 8.7 Hz), 7.19-7.13 (2H, m), 4.36-4.28 (2H, m), 4.07-4.00 (2H, m), 2.52 (3H, s). LCMS (ES+) 355.1 and 357.0 (M+H)$^+$, RT 3.73 minutes (Method 7).

EXAMPLE 29

Method 1

2-(7-Bromo-2,3-dihydro-4H-1,4-benzoxazin-4-yl)-N,4-dimethyl-1,3-thiazole-5-carboxamide To a stirred solution of Example 28 (0.35 g, 0.99 mmol) in DCM (10 mL) were added 1-hydroxybenzotriazole hydrate (0.015 g, 0.11 mmol), DIPEA (0.175 mL, 1.00 mmol) and EDC (210 mg, 1.08 mmol). The reaction mixture was stirred at r.t. for 5 minutes. Methylamine (0.185 mL, 33% wt. solution in EtOH, 1.97 mmol) was added and stirring was continued at r.t. for 20 h. The reaction mixture was then diluted with DCM (100 mL) and then washed with sat. aqueous NaHCO$_3$ solution (100 mL), then water (100 mL) and brine (100 mL). The organic fraction was dried (NaSO$_4$), filtered and concentrated in vacuo. Purification by column chromatography (SiO$_2$, 0-10% MeOH/DCM) gave the title compound (0.22 g, 61%) as a white solid. $\delta_H$ (DMSO-d$_6$) 8.07 (1H, d, J 8.5 Hz), 7.83-7.75 (1H, m), 7.19-7.12 (2H, m), 4.34-4.27 (2H, m), 4.04-3.97 (2H, m), 2.70 (3H, d, J 4.5 Hz), 2.47 (3H, s). LCMS (ES+) 368.1 and 370.1 (M+H)$^+$, RT 3.50 minutes (Method 7).

EXAMPLE 30

2-(7-Bromo-2,3-dihydro-4H-1,4-benzoxazin-4-yl)-N,N,4-trimethyl-1,3-thiazole-5-carboxamide The title compound was prepared from Example 28 and dimethylamine (2M solution in THF) according to Method I and was isolated as a clear glass (77%) after purification by column chromatography (SiO$_2$, 3-9% MeOH/DCM). $\delta_H$ (DMSO-d$_6$) 8.14 (1H, d, J 8.7 Hz), 7.18-7.11 (2H, m), 4.34-4.28 (2H, m), 4.01-3.96 (2H, m), 2.98 (6H, s), 2.24 (3H, s). LCMS (ES+) 382.1 and 384.0 (M+H)$^+$, RT 3.63 minutes (Method 7).

EXAMPLE 31

Method J

N,4-Dimethyl-2-{7-[N-methyl-N-(1-methylpiperidin-4-yl)amino]-2,3-dihydro-4H-1,4-benzoxazin-4-yl}-1,3-thiazole-5-carboxamide formate A mixture of Example 29 (0.085 g, 0.23 mmol), 1-methyl-4-(methylamino)-piperidine (0.067 mL, 0.46 mmol), di-µ-bromobis(tri-tert-butylphosphino)dipalladium(I) (0.018 g, 0.023 mmol) and sodium tert-butoxide (67 mg, 0.69 mmol) in toluene (2.0 mL) was heated to 110° C. under microwave irradiation, in a sealed tube, for 1 h. The reaction mixture was then cooled to r.t. and partitioned between DCM (50 mL) and water (50 mL). The organic fraction was dried (NaSO$_4$), filtered and concentrated in vacuo. Purification by preparative HPLC (Method 5) gave the title compound (0.007 g, 7%) as a white solid. $\delta_H$ (CDCl$_3$) 8.48 (1H, s, formic acid), 7.57 (1H, d, J 8.9 Hz), 6.43-6.38 (1H, m), 6.37-6.33 (1H, m), 5.56-5.49 (1H, m), 4.29-4.23 (2H, m), 4.14-4.08 (2H, m), 3.74-3.61 (1H, m), 3.50-3.40 (2H, m), 2.93 (3H, d, J 4.9 Hz), 2.77 (3H, s), 2.62 (3H, s), 2.61-2.58 (2H, m), 2.56 (3H, s), 2.31-2.14 (2H, m), 1.90-1.79 (2H, m). LCMS (ES+) 416.2 (M+H)$^+$, RT 1.63 minutes (Method 7).

EXAMPLE 32

N,N,4-Trimethyl-2-{7-[N-methyl-N-(1-methylpiperidin-4-yl)amino]-2,3-dihydro-4H-1,4-benzoxazin-4-yl}-1,3-thiazole-5-carboxamide formate The title compound was prepared from Example 30 and 1-methyl-4-(methyl-amino)piperidine according to Method J and was isolated as a white solid (40%) after purification by preparative HPLC (Method 5). $\delta_H$ (CDCl$_3$) 8.48 (1H, s, formic acid), 7.59 (1H, d, J 9.0 Hz), 6.43-6.33 (2H, m), 4.29-4.23 (2H, m), 4.11-4.05 (2H, m), 3.71-3.59 (1H, m), 3.46-3.36 (2H, m), 3.07 (6H, s), 2.76 (3H, s), 2.59 (3H, s), 2.57-2.48

(2H, m), 2.31 (3H, s), 2.25-2.09 (2H, m), 1.88-1.78 (2H, m). LCMS (ES+) 430.2 (M+H)$^+$, RT 1.68 minutes (Method 7).

The invention claimed is:

1. A compound of formula (I), or a pharmaceutically acceptable salt thereof:

(I)

wherein
- $R^1$ represents —COR$^a$ or —CONR$^b$R$^c$;
- $R^a$ represents $C_{1-6}$ alkyl;
- $R^b$ represents hydrogen, $C_{1-6}$ alkyl, $C_{3-7}$ cycloalkyl or $C_{3-7}$ cycloalkyl($C_{1-6}$)alkyl;
- $R^c$ represents hydrogen or $C_{1-6}$ alkyl;
- $R^2$ represents hydrogen, $C_{1-6}$ alkyl, halogen, cyano or trifluoromethyl;
- $R^3$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; and
- $R^4$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; or
- $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or
- $R^3$ and $R^4$, when attached to adjacent carbon atoms, represent, when taken together with the carbon atoms to which they are attached, $C_{5-7}$ cycloalkyl, phenyl, $C_{5-7}$ heterocycloalkyl or heteroaryl, any of which groups may be optionally benzo-fused and/or substituted by one or more substituents.

2. A compound as claimed in claim 1 represented by formula (IIA), or a pharmaceutically acceptable salt thereof:

(IIA)

wherein
- $R^1$ and $R^2$ are as defined in claim 1; and
- $R^{13}$ represents $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

3. A compound as claimed in claim 2 represented by formula (IIB), or a pharmaceutically acceptable salt thereof:

(IIB)

wherein
- $R^1$ and $R^2$ are as defined in claim 1;
- $R^{23}$ represents hydrogen, halogen, cyano, nitro, $C_{1-6}$ alkyl, hydroxy($C_{1-6}$)alkyl, trifluoromethyl, aryl($C_{1-6}$)alkyl, triazolyl, hydroxy, $C_{1-6}$ alkoxy, difluoromethoxy, trifluoromethoxy, aryloxy, aryl($C_{1-6}$)alkoxy, $C_{1-6}$ alkylthio, $C_{1-6}$ alkylsulphinyl, arylsulphinyl, $C_{1-6}$ alkylsulphonyl, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl, trifluoroacetyl, carboxy, $C_{2-6}$ alkoxycarbonyl, aminocarbonyl, $C_{1-6}$ alkylaminocarbonyl, [hydroxy-($C_{1-6}$)alkyl]aminocarbonyl, di($C_{1-6}$)alkylaminocarbonyl, [($C_{1-6}$)alkyl][hydroxy-($C_{1-6}$)alkyl]aminocarbonyl, aryl($C_{1-6}$)alkylaminocarbonyl, azetidinylcarbonyl, pyrrolidinylcarbonyl, piperidinylcarbonyl, ($C_{1-6}$)alkylpiperazinylcarbonyl or morpholinylcarbonyl; and
- $R^{24}$ represents hydrogen, halogen, $C_{1-6}$ alkoxy or di($C_{1-6}$)alkylaminocarbonyl; or
- $R^{23}$ and $R^{24}$, when situated on adjacent carbon atoms, together represent methylenedioxy or difluoromethylenedioxy; and
- $R^{25}$ represents hydrogen or $C_{1-6}$ alkyl.

4. A compound as claimed in claim 2 represented by formula (IIC), or a pharmaceutically acceptable salt thereof:

(IIC)

wherein
- $R^1$ and $R^2$ are as defined in claim 1;
- $R^{33}$ represents halogen or —NHR$^{34}$; or aryl or heteroaryl, either of which groups may be optionally substituted by one or more substituents; and
- $R^{34}$ represents phenyl, pyridinyl, halopyridinyl, ($C_{1-6}$)alkylpyridinyl, di($C_{1-6}$)alkylpyridinyl or ($C_{1-6}$)alkoxypyridinyl.

5. A compound as claimed in claim 1 represented by formula (IID-1) or (IID-2), or a pharmaceutically acceptable salt thereof:

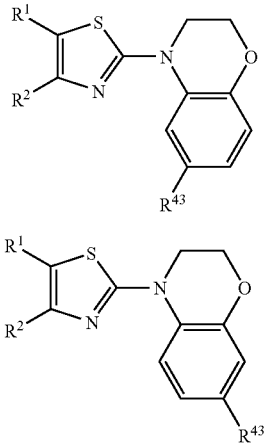

wherein
R¹ and R² are as defined above; and
R⁴³ represents hydrogen, halogen, nitro, hydroxy($C_{1-6}$) alkyl, piperidinyl($C_{1-6}$)alkyl-phenyl, pyrazolyl, ($C_{1-6}$) alkylpyrazolyl, di($C_{1-6}$)alkylpyrazolyl, aryl($C_{1-6}$)alkylpyrazolyl, morpholinyl($C_{1-6}$)alkylpyrazolyl, imidazolyl, ($C_{1-6}$)alkylimidazolyl, pyridinyl, ($C_{1-6}$) alkyl-pyridinyl, pyrimidinyl, hydroxy, pyridinyloxy($C_{1-6}$)alkyl, amino, pyridinylamino, halopyridinylamino, ($C_{1-6}$)alkylpyridinylamino, di($C_{1-6}$)alkylpyridinylamino, ($C_{1-6}$)alkoxy-pyridinylamino, N—($C_{1-6}$) alkyl-N—[($C_{1-6}$)alkylpiperidinyl]amino, amino($C_{1-6}$) alkyl, ($C_{1-6}$)alkylamino($C_{1-6}$)alkyl, di($C_{1-6}$)alkylamino ($C_{1-6}$)alkyl, pyridinylamino($C_{1-6}$)alkyl, ($C_{1-6}$) alkylpiperazinyl($C_{1-6}$)alkyl, morpholinyl($C_{1-6}$)alkyl, formyl or $C_{2-6}$ alkoxycarbonyl-oxy.

6. A compound selected from the group consisting of:
2-[(3S)-3-(1H-indol-3-ylmethyl)morpholin-4-yl]-4-methyl-1,3-thiazole-5-carboxamide;
N-cyclopropyl-2-[(3S)-3-(1H-indol-3-ylmethyl)morpholin-4-yl]-4-methyl-1,3-thiazole-5-carboxamide;
1-{2-[(3S)-3-(1H-indol-3-ylmethyl)morpholin-4-yl]-4-methyl-1,3-thiazol-5-yl}ethanone;
4-methyl-2-[(3S)-3-{[5-(trifluoromethoxy)-1H-indol-3-yl]methyl}morpholin-4-yl]-1,3-thiazole-5-carboxamide;
methyl 3-{[(3S)-4-(5-carbamoyl-4-methyl-1,3-thiazol-2-yl)morpholin-3-yl]methyl}-1H-indole-5-carboxylate;
methyl 3-{[(3S)-4-(5-acetyl-4-methyl-1,3-thiazol-2-yl)morpholin-3-yl]methyl}-1H-indole-5-carboxylate;
methyl 3-{[(3S)-4-(5-acetyl-4-methyl-1,3-thiazol-2-yl)morpholin-3-yl]methyl}-1H-indole-6-carboxylate;
1-(2-{(3R)-3-[(3-bromophenoxy)methyl]morpholin-4-yl}-4-methyl-1,3-thiazol-5-yl)ethanone;
1-{2-[(3S)-3-(3-bromobenzyl)morpholin-4-yl]-4-methyl-1,3-thiazol-5-yl}ethanone;
2-[(3S)-3-(3-bromobenzyl)morpholin-4-yl]-4-methyl-1,3-thiazole-5-carboxamide;
3-{[(3S)-4-(5-acetyl-4-methyl-1,3-thiazol-2-yl)morpholin-3-yl]methyl}-1H-indole-5-carboxylic acid;
3-{[(3S)-4-(5-acetyl-4-methyl-1,3-thiazol-2-yl)morpholin-3-yl]methyl}-N,N-dimethyl-1H-indole-5-carboxamide;
1-(4-methyl-2-{(3S)-3-[3-(pyridin-4-ylamino)benzyl]morpholin-4-yl}-1,3-thiazol-5-yl)ethanone;
1-{2-[(3S)-3-(3-anilinobenzyl)morpholin-4-yl]-4-methyl-1,3-thiazol-5-yl}ethanone;
1-(4-methyl-2-{(3S)-3-[3-(pyridin-3-yl)benzyl]morpholin-4-yl}-1,3-thiazol-5-yl)-ethanone;
1-[2-(6-bromo-2,3-dihydro-4H-benzo[1,4]oxazin-4-yl)-4-methyl-1,3-thiazol-5-yl]-ethanone;
3-{[(3S)-4-(5-acetyl-4-methyl-1,3-thiazol-2-yl)morpholin-3-yl]methyl}-1H-indole-5-carbonitrile;
1-(2-{(3S)-[(6-methoxy-1H-indol-3-yl)methyl]morpholin-4-yl}-4-methyl-1,3-thiazol-5-yl)ethanone;
1-(2-{(3S)-3-[(5-acetyl-b 1H-indol-3-yl)methyl]morpholin-4-yl}-4-methyl-1,3-thiazol-5-yl)ethanone;
1-(2-{(3S)-3-[(2,2-difluoro-5H-[1,3]dioxolo[4,5-f]indol-7-yl)methyl]morpholin-4-yl}-4-methyl-1,3-thiazol-5-yl)ethanone;
1-(3-{[(3S)-4-(5-acetyl-4-methyl-1,3-thiazol-2-yl)morpholin-3-yl]methyl}-1H-indol-5-yl)-2,2,2-trifluoroethanone;
1-{2-[(3S)-3-(5H-[1,3]dioxolo[4,5-f]indol-7-ylmethyl)morpholin-4-yl]-4-methyl-1,3-thiazol-5-yl}ethanone;
1-(2-{(3S)-3-[(5,6-dimethoxy-1H-indol-3-yl)methyl]morpholin-4-yl}-4-methyl-1,3-thiazol-5-yl)ethanone;
1-{4-methyl-2-[(3S)-3-{[5-(methylsulfonyl)-1H-indol-3-yl]methyl}morpholin-4-yl]-1,3-thiazol-5-yl}ethanone;
1-{4-methyl-2-[(3S)-3-{[5-(1H-1,2,4-triazol-1-yl)-1H-indol-3-yl]methyl}morpholin-4-yl]-1,3-thiazol-5-yl}ethanone;
1-(4-methyl-2-{7-[N-methyl-N-(1-methylpiperidin-4-yl)amino]-2,3-dihydro-4H-1,4-benzoxazin-4-yl}-1,3-thiazol-5-yl)ethanone;
1-(4-methyl-2-{6-[3-(piperidin-1-ylmethyl)phenyl]-2,3-dihydro-4H-1,4-benzoxazin-4-yl}-1,3-thiazol-5-yl)ethanone, acetic acid salt;
2-(7-bromo-2,3-dihydro-4H-1,4-benzoxazin-4-yl)-N,4-dimethyl-1,3-thiazole-5-carboxamide;
2-(7-bromo-2,3-dihydro-4H-1,4-benzoxazin-4-yl)-N,N,4-trimethyl-1,3-thiazole-5-carboxamide;
N,4-dimethyl-2-{7-[N-methyl-N-(1-methylpiperidin-4-yl)amino]-2,3-dihydro-4H-1,4-benzoxazin-4-yl}-1,3-thiazole-5-carboxamide formate; and
N,N,4-trimethyl-2-{7-[N-methyl-N-(1-methylpiperidin-4-yl)amino]-2,3-dihydro-4H-1,4-benzoxazin-4-yl}-1,3-thiazole-5-carboxamide formate.

7. A pharmaceutical composition comprising a compound of formula (I) as defined in claim 1, or a pharmaceutically acceptable salt thereof, in association with a pharmaceutically acceptable carrier.

* * * * *